United States Patent
Mio et al.

(10) Patent No.: US 9,227,950 B2
(45) Date of Patent: Jan. 5, 2016

(54) CYCLIC SULFATE COMPOUND, NON-AQUEOUS ELECTROLYTE SOLUTION CONTAINING SAME, AND LITHIUM SECONDARY BATTERY

(75) Inventors: Shigeru Mio, Chiba (JP); Mitsuo Nakamura, Chosei-gun (JP); Kaichiro Haruta, Ichihara (JP); Hidenobu Nogi, Chiba (JP); Satoko Fujiyama, Kisarazu (JP); Takashi Hayashi, Ichihara (JP); Hidetoshi Tsunoda, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 367 days.

(21) Appl. No.: 13/820,969

(22) PCT Filed: Oct. 21, 2011

(86) PCT No.: PCT/JP2011/074339
§ 371 (c)(1),
(2), (4) Date: Mar. 5, 2013

(87) PCT Pub. No.: WO2012/053644
PCT Pub. Date: Apr. 26, 2012

(65) Prior Publication Data
US 2013/0171514 A1 Jul. 4, 2013

(30) Foreign Application Priority Data

Oct. 22, 2010 (JP) ................................ 2010-237173
Aug. 31, 2011 (JP) ................................ 2011-189632

(51) Int. Cl.
| | | |
|---|---|---|
| H01M 2/34 | (2006.01) | |
| C07D 327/10 | (2006.01) | |
| H01M 10/0525 | (2010.01) | |
| H01M 10/0567 | (2010.01) | |

(52) U.S. Cl.
CPC ......... *C07D 327/10* (2013.01); *H01M 10/0525* (2013.01); *H01M 10/0567* (2013.01); *Y02E 60/122* (2013.01); *Y02T 10/7011* (2013.01)

(58) Field of Classification Search
CPC ............. H01M 10/0525; H01M 10/0567; C07D 327/10; Y02E 60/122; Y02T 10/7011

USPC ........................................................ 429/200
See application file for complete search history.

(56) References Cited

U.S. PATENT DOCUMENTS

| | | | |
|---|---|---|---|
| 2004/0137332 A1* | 7/2004 | Noh et al. ..................... | 429/329 |
| 2009/0280414 A1 | 11/2009 | Koh et al. | |

FOREIGN PATENT DOCUMENTS

| | | |
|---|---|---|
| JP | 10-189042 A | 7/1998 |
| JP | 2003-151623 A | 5/2003 |
| JP | 2003-308875 A | 10/2003 |
| JP | 2004-022523 A | 1/2004 |
| JP | 2005-011762 A | 1/2005 |
| JP | 2001-501183 A | 1/2006 |
| JP | 2006-140115 A | 6/2006 |
| JP | 2009-140921 A | 6/2009 |
| JP | 2010-503974 A | 2/2010 |
| WO | WO 2011/122449 A1 | 10/2011 |

OTHER PUBLICATIONS

Japan Office Action (Notice of Reasons for Rejection) dated Jan. 28, 2014, issued in corresponding Japanese Patent Application No. 2012-539785 with an English translation thereof. (4 pgs).
Marson, C. M., et al. "Synthesis of (3S,3S',4S,4S')-1,1-ethylenedipyrrolidine-3,3 ,4,4-tetraol and related diamino diols: donor-acceptor hydrogen-bonding motifs of the $C_2$ symmetric 3,4-dihydroxypyrrolidine Unit", *Tetrahedronasymmetry* 16, 2005, pp. 2799-2809.
International Search Report (PCT/ISA/210) issued on Jan. 17, 2012, by the Japanese Patent Office as the International Searching Authority for International Application No. PCT/JP2011/074339.
Written Opinion (PCT/ISA/237) issued on Jaury 17, 2012, by the Japanese Patent Office as the International Searching Authority for International Application No. PCT/JP2011/074339.
V. Glacon et al., "Heterocyclisation of free or partially protected alditols via their bis-cyclic sulfate derivates. Versatile synthesis of aza and thiodeoxyanhydroalditol with *erythro, threo, arabino, gulo, talo* or *manno* configuration", Tetrahedron Letters, 2000, pp. 5053-5056, vol. 41.

* cited by examiner

*Primary Examiner* — Jonathan Jelsma
*Assistant Examiner* — Rashid Alam
(74) *Attorney, Agent, or Firm* — Buchanan, Ingersoll & Rooney PC

(57) ABSTRACT

A non-aqueous electrolyte solution containing a cyclic sulfate compound represented by formula (I) is provided, wherein in formula (I), $R^1$ represents a group represented by formula (II) or a group represented by formula (III); $R^2$ represents a hydrogen atom, an alkyl group having from 1 to 6 carbon atoms, a group represented by formula (II), or a group represented by formula (III); and in formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV).
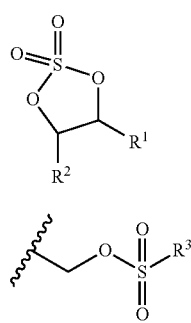
(I)
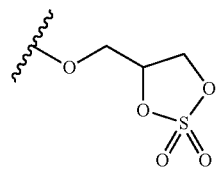
(III)
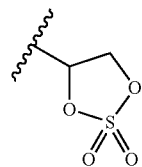
(II)
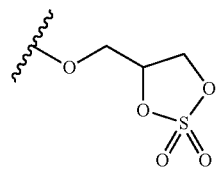
(IV)
18 Claims, 1 Drawing Sheet

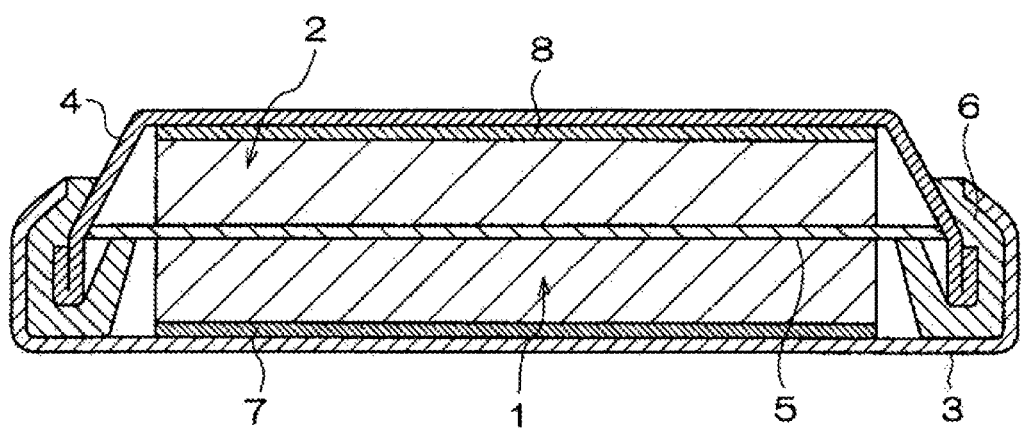

CYCLIC SULFATE COMPOUND, NON-AQUEOUS ELECTROLYTE SOLUTION CONTAINING SAME, AND LITHIUM SECONDARY BATTERY

TECHNICAL FIELD

The present invention relates to a non-aqueous electrolyte solution having an excellent performance of maintaining the open circuit voltage during the storage of a battery in a charged state, a lithium secondary battery using the electrolyte solution, an additive for lithium secondary batteries which is useful as an additive for electrolyte solutions, and a cyclic sulfate compound suitable for the additive.

BACKGROUND ART

In recent years, lithium secondary batteries are widely used as power sources for electronic devices such as mobile telephones and notebook computers, or for electric cars or electric power storage. Particularly recently, there is a rapidly increasing demand for a high capacity and high power battery with a high energy density, which can be mounted in hybrid cars or electric cars.

Lithium secondary batteries are primarily composed of a positive electrode and a negative electrode, which contain materials capable of absorption and desorption of lithium, and a non-aqueous electrolyte solution containing a lithium salt and a non-aqueous solvent.

Examples of positive electrode active materials used in a positive electrode include lithium metal oxides such as $LiCoO_2$, $LiMnO_2$, $LiNiO_2$, and $LiFePO_4$.

Furthermore, as the non-aqueous electrolyte solution, solutions prepared by mixing a mixed solvent (non-aqueous solvent) of carbonates such as ethylene carbonate, propylene carbonate, ethylene carbonate or methyl carbonate, with a Li electrolyte such as $LiPF_6$, $LiBF_4$, $LiN(SO_2CF_3)_2$ or $LiN(SO_2CF_2CF_3)_2$, are used.

On the other hand, as the active material for a negative electrode that is used in negative electrodes, metal lithium, metal compounds (elemental metals, oxides, alloys with lithium, and the like) capable of absorption and desorption of lithium, and carbon materials are known. Particularly, lithium secondary batteries employing cokes, artificial graphite or natural graphite, which are all capable of absorption and desorption of lithium, have been put to practical use.

Among the battery performances, particularly in relation to lithium secondary batteries for automotive applications, an increase in output power and an increase in service life are required. It has been a considerable challenge to achieve a balance between a reduction of the resistance of a battery under various conditions and an enhancement of the service life performance of a battery.

One of the factors known to cause an increase in the resistance of a battery is a passivation film based on a solvent decomposition product or an inorganic salt, which is formed on the surface of a negative electrode. In general, it is known that since lithium metal is present among the negative electrode active material under the charging conditions, a reductive decomposition reaction of the electrolyte solution occurs at the surface of the negative electrode. In a case in which such reductive decomposition continuously occurs, the resistance of the battery increases, the charge-discharge efficiency decreases, and the energy density of the battery decreases. Furthermore, on the other hand, it is also known in regard to the positive electrode that a deterioration reaction occurs over time, the resistance continually increases, and a decrease in the battery performance is caused. In order to overcome these problems, attempts have been made to add various compounds to electrolyte solution.

As a trial for the purpose, it has been attempted to improve the battery performance by incorporating various cyclic sulfate compounds (see, for example, Japanese Patent Application Laid-Open (JP-A) No. 10-189042, JP-A No. 2003-151623, JP-A No. 2003-308875, JP-A No. 2004-22523, and JP-A No. 2005-011762).

SUMMARY OF INVENTION

Technical Problem

It is believed that by adding the cyclic sulfates having lower alkyl groups, which are described in the various documents mentioned above, dense passivation films are formed on negative electrodes, and as the reaction between the organic solvent in the electrolyte solution and the negative electrode is continuously suppressed by these passivation films, retention of the battery capacity is brought about.

However, it has been found that when those cyclic sulfates having lower alkyl groups as described in the various documents mentioned above are added, there occurs a new problem that the potential in a charged state is lowered (more particularly, the open circuit voltage decreases during the storage of a battery in a charged state).

The invention was achieved in order to cope with the problem described above, and it is an object of the invention to provide a non-aqueous electrolyte solution which can significantly suppress a decrease in the open circuit voltage during the storage of a battery in a charged state, while improving the capacity retention performance of the battery, and a lithium secondary battery using the non-aqueous electrolyte solution.

It is another object of the invention to provide an additive for lithium secondary batteries which is useful for such a non-aqueous electrolyte solution, and a cyclic sulfate compound which is useful as an additive for non-aqueous electrolyte solutions.

Solution to Problem

The inventors of the invention have conducted a thorough investigation in connection with the problems described above, and as a result, the inventors found that when a particular compound is added to a non-aqueous electrolyte solution for lithium secondary batteries, a decrease in potential (a decrease in the open circuit voltage during the storage of a battery in a charged state) can be markedly suppressed, while the capacity retention performance is improved. Thus, the inventors completed the invention.

That is, the means for solving the problems of the invention are as follows.

<1> A non-aqueous electrolyte solution, comprising:
a cyclic sulfate compound represented by the following formula (I).

-continued

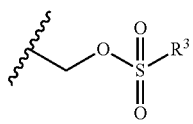
(II)

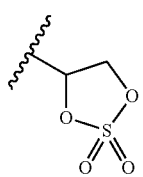
(III)

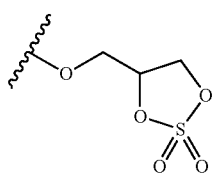
(IV)

In formula (I), $R^1$ represents a group represented by the above formula (II) or a group represented by the above formula (III); and $R^2$ represents a hydrogen atom, an alkyl group having from 1 to 6 carbon atoms, a group represented by formula (II), or a group represented by formula (III).

In formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding.

In a case in which there are two groups represented by formula (II) in the cyclic sulfate compound represented by formula (I), the two groups represented by formula (II) may be the same as or different from each other.

<2> The non-aqueous electrolyte solution described in item <1>, wherein in formula (I), $R^1$ represents a group represented by formula (II) (provided that in formula (II), $R^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III); and $R^2$ represents a hydrogen atom, an alkyl group having from 1 to 3 carbon atoms, a group represented by formula (II) (provided that in formula (II), $R^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

<3> The non-aqueous electrolyte solution described in item <1> or <2>, wherein in formula (I), $R^1$ represents a group represented by formula (II) (provided that in formula (II), $R^3$ represents a fluorine atom, a methyl group, an ethyl group, a methoxy group, an ethoxy group, or a group represented by formula (IV)), or a group represented by formula (III); and $R^2$ represents a hydrogen atom or a methyl group.

<4> The non-aqueous electrolyte solution described in any one of items <1> to <3>, wherein in formula (I), $R^1$ represents a group represented by formula (III), and $R^2$ represents a hydrogen atom.

<5> The non-aqueous electrolyte solution described in any one of items <1> to <4>, further comprising at least one of an electrolyte compound represented by the following formula (V) or lithium difluorophosphate.

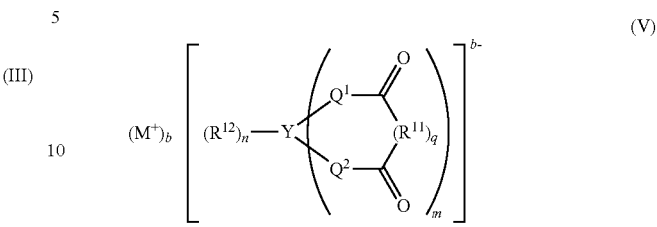
(V)

In formula (V), M represents an alkali metal; Y represents a transition element, or an element of Group 13, Group 14 or Group 15 of the Periodic Table of Elements; b represents an integer from 1 to 3; m represents an integer from 1 to 4; n represents an integer from 0 to 8; q represents 0 or 1; $R^{11}$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, wherein such groups may each contain a substituent or a heteroatom in the structure, and when q is 1 and m is 2 to 4, m units of $R^{11}$ may be bonded to each other; $R^{12}$ represents a halogen atom, an alkyl group having from 1 to 10 carbon atoms, a halogenated alkyl group having from 1 to 10 carbon atoms, an aryl group having from 6 to 20 carbon atoms, a halogenated aryl group having from 6 to 20 carbon atoms, or $-Q^3R^{13}$, wherein such groups, other than $-Q^3R^{13}$, may each contain a substituent or a heteroatom in the structure, and when n represents an integer from 2 to 8, n units of $R^{12}$ may be bonded to each other to form a ring; $Q^1$, $Q^2$, and $Q^3$ each independently represent O, S or $NR^{14}$; and $R^{13}$ and $R^{14}$ each independently represent a hydrogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, wherein such groups may each contain a substituent or a heteroatom in the structure, and when plural $R^{13}$'s or plural $R^{14}$'s are present, the respective groups may be bonded to each other to form a ring.

<6> The non-aqueous electrolyte solution described in item <5>, wherein the electrolyte compound represented by formula (V) is at least one compound selected from the group consisting of a compound represented by the following formula (VI), a compound represented by the following formula (VII), a compound represented by the following formula (VIII), and a compound represented by the following formula (IX).

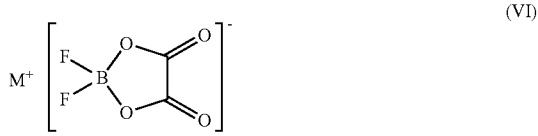
(VI)

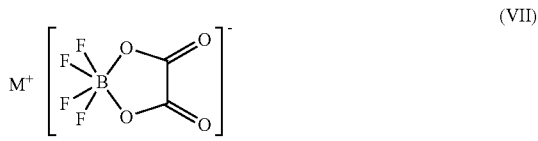
(VII)

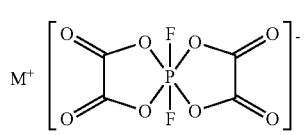 (VIII)

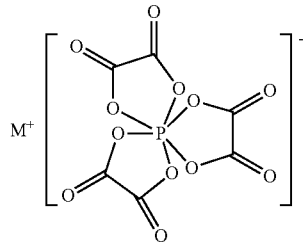 (IX)

In formulae (VI) to (IX), M has the same definition as M in formula (V).

<7> The non-aqueous electrolyte solution described in any one of items <1> to <6>, further comprising a compound represented by the following formula (X).

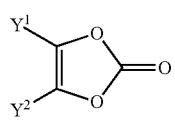 (X)

In formula (X), $Y^1$ and $Y^2$ each independently represent a hydrogen atom, a methyl group, an ethyl group, or a propyl group.

<8> The non-aqueous electrolyte solution described in any one of items <1> to <7>, further comprising a compound represented by the following formula (XI).

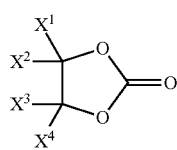 (XI)

In formula (XI), $X^1$, $X^2$, $X^3$ and $X^4$ each independently represent an alkyl group, having from 1 to 3 carbon atoms, that may be substituted with a fluorine atom; a hydrogen atom; a fluorine atom; or a chlorine atom, provided that $X^1$ to $X^4$ are not both hydrogen atoms at the same time.

<9> The non-aqueous electrolyte solution described in any one of items <1> to <8>, wherein the content of the cyclic sulfate compound represented by formula (I) is from 0.001 mass % to 10 mass %.

<10> The non-aqueous electrolyte solution described in any one of items <5> to <9>, wherein the content of at least one of the electrolyte compound represented by formula (V) or the lithium difluorophosphate is from 0.001 mass % to 10 mass %.

<11> The non-aqueous electrolyte solution described in any one of items <7> to <10>, wherein the content of the compound represented by formula (X) is from 0.001 mass % to 10 mass %.

<12> The non-aqueous electrolyte solution described in any one of items <8> to <11>, wherein the content of the compound represented by formula (XI) is from 0.001 mass % to 10 mass %.

<13> An additive for a lithium secondary battery, the additive comprising a cyclic sulfate compound represented by the following formula (I) as an active ingredient.

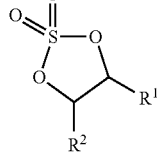 (I)

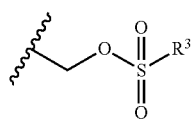 (II)

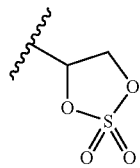 (III)

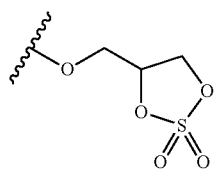 (IV)

In formula (I), $R^1$ represents a group represented by the above formula (II) or a group represented by the above formula (III); and $R^2$ represents a hydrogen atom, an alkyl group having from 1 to 6 carbon atoms, a group represented by formula (II), or a group represented by formula (III).

In formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding.

In a case in which there are two groups represented by formula (II) in the cyclic sulfate compound represented by formula (I), the two groups represented by formula (II) may be the same as or different from each other.

<14> A cyclic sulfate compound represented by the following formula (I).

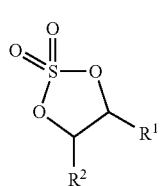 (I)

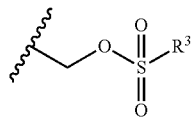 (II)

-continued

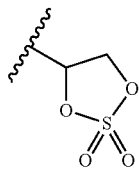
(III)

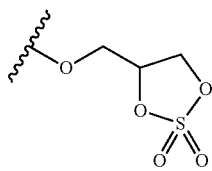
(IV)

In formula (I), $R^1$ represents a group represented by the above formula (II) or a group represented by the above formula (III); and $R^2$ represents a hydrogen atom, an alkyl group having from 1 to 6 carbon atoms, a group represented by formula (II), or a group represented by formula (III).

In formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding.

In a case in which there are two groups represented by formula (II) in the cyclic sulfate compound represented by formula (I), the two groups represented by formula (II) may be the same as or different from each other.

<15> The cyclic sulfate compound described in item <14>, which is represented by the following formula (XII).

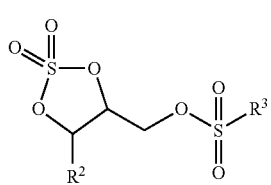
(XII)

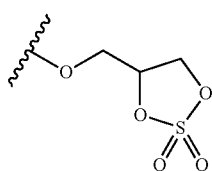
(IV)

In formula (XII), $R^2$ represents a hydrogen atom or an alkyl group having from 1 to 6 carbon atoms; and $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV).

<16> The cyclic sulfate compound described in item <15>, wherein in formula (XII), $R^2$ represents a hydrogen atom or a methyl group; and $R^3$ represents a fluorine atom, a methyl group, an ethyl group, a methoxy group, an ethoxy group, or a group represented by formula (IV).

<17> The cyclic sulfate compound described in item <15>, which is 4-methylsulfonyloxymethyl-2,2-dioxo-1,3,2-dioxathiolane, 4-ethylsulfonyloxymethyl-2,2-dioxo-1,3,2-dioxathiolane, or bis((2,2-dioxo-1,3,2-dioxathiolane-4-yl)methyl) sulfate.

<18> A lithium secondary battery, comprising:
a positive electrode;
a negative electrode including, as a negative electrode active material, at least one selected from metal lithium, a lithium-containing alloy, a metal or alloy capable of alloying with lithium, an oxide capable of doping and dedoping of lithium ions, transition metal nitrides capable of doping and dedoping of lithium ions, or a carbon material capable of doping and dedoping of lithium ions; and
the non-aqueous electrolyte solution described in any one of items <1> to <12>.

<19> A lithium secondary battery obtained by charging or discharging a lithium secondary battery that includes: a positive electrode; a negative electrode containing, as a negative electrode active material, at least one selected from metal lithium, a lithium-containing alloy, a metal or alloy capable of alloying with lithium, an oxide capable of doping and dedoping of lithium ions, transition metal nitrides capable of doping and dedoping of lithium ions, or a carbon material capable of doping and dedoping of lithium ions; and the non-aqueous electrolyte solution described in any one of items <1> to <12>.

Advantageous Effects of Invention

According to the invention, a non-aqueous electrolyte solution which is used in lithium secondary batteries, and can markedly suppress a decrease in the open circuit voltage during the storage of a battery in a charged state, while improving the capacity retention performance of the battery, and a lithium secondary battery using the non-aqueous electrolyte solution can be provided.

Furthermore, according to the invention, an additive for lithium secondary batteries which is useful for such a non-aqueous electrolyte solution, and a novel cyclic sulfate compound which is useful as an additive for non-aqueous electrolyte solutions can be provided.

BRIEF DESCRIPTION OF DRAWINGS

FIG. 1 is a schematic cross-sectional diagram of a coin cell illustrating an example of the lithium secondary battery of the invention.

DESCRIPTION OF EMBODIMENTS

The cyclic sulfate compound of the invention, a non-aqueous electrolyte solution using the compound, an additive for lithium secondary batteries, and a lithium secondary battery will be described specifically.

[Cyclic Sulfate Compound Represented by Formula (I)]
The cyclic sulfate compound of the invention is a cyclic sulfate compound represented by the following formula (I).

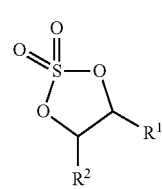
(I)

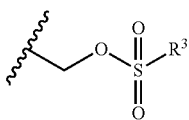
(II)

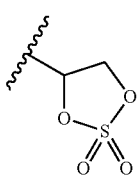
(III)

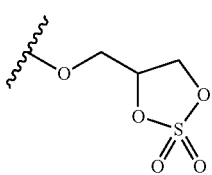
(IV)

In formula (I), $R^1$ represents a group represented by the above formula (II) or a group represented by the above formula (III); and $R^2$ represents a hydrogen atom, an alkyl group having from 1 to 6 carbon atoms, a group represented by formula (II), or a group represented by formula (III).

In formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding.

In a case in which there are two groups represented by formula (II) in the cyclic sulfate compound represented by formula (I), the two groups represented by formula (II) may be the same as or different from each other.

In formula (I), specific examples of the "halogen atom" include a fluorine atom, a chlorine atom, a bromine atom, and an iodine atom.

The halogen atom is preferably a fluorine atom.

In formula (I), the "alkyl group having from 1 to 6 carbon atoms" is a linear or branched alkyl group having from 1 to 6 carbon atoms, and specific examples thereof include a methyl group, an ethyl group, a propyl group, an isopropyl group, a butyl group, an isobutyl group, a sec-butyl group, a tert-butyl group, a pentyl group, a 2-methylbutyl group, a 1-methylpentyl group, a neopentyl group, a 1-ethylpropyl group, a hexyl group, and a 3,3-dimethylbutyl group.

The alkyl group having from 1 to 6 carbon atoms is more preferably an alkyl group having from 1 to 3 carbon atoms.

In formula (I), the "halogenated alkyl group having from 1 to 6 carbon atoms" is a linear or branched halogenated alkyl group having from 1 to 6 carbon atoms, and specific examples thereof include a fluoromethyl group, a difluoromethyl group, a trifluoromethyl group, a 2,2,2-trifluoroethyl group, a perfluoroethyl group, a perfluoropropyl group, a perfluorobutyl group, a perfluoropentyl group, a perfluorohexyl group, a perfluoroisopropyl group, a perfluoroisobutyl group, a chloromethyl group, a chloroethyl group, a chloropropyl group, a bromomethyl group, a bromoethyl group, a bromopropyl group, an iodomethyl group, an iodoethyl group, and an iodopropyl group.

The halogenated alkyl group having from 1 to 6 carbon atoms is more preferably a halogenated alkyl group having from 1 to 3 carbon atoms.

In formula (I), the "alkoxy group having from 1 to 6 carbon atoms" is a linear or branched alkoxy group having from 1 to 6 carbon atoms, and specific examples thereof include a methoxy group, an ethoxy group, a propoxy group, an isopropoxy group, a butoxy group, an isobutoxy group, a sec-butoxy group, a tert-butoxy group, a pentyloxy group, a 2-methylbutoxy group, a 1-methylpentyloxy group, a neopentyloxy group, a 1-ethylpropoxy group, a hexyloxy group, and a 3,3-dimethylbutoxy group.

The alkoxy group having from 1 to 6 carbon atoms is more preferably an alkoxy group having from 1 to 3 carbon atoms.

$R^1$ in formula (I) is preferably a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

$R^2$ in formula (I) is preferably a hydrogen atom, an alkyl group having from 1 to 3 carbon atoms, a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III), and more preferably a hydrogen atom or a methyl group. $R^2$ is particularly preferably a hydrogen atom.

In a case in which $R^1$ in formula (I) is a group represented by formula (II), $R^3$ in formula (II) is a halogen atom, an alkyl group having from 1 to 6 carbon atoms, a halogenated alkyl group having from 1 to 6 carbon atoms, an alkoxy group having from 1 to 6 carbon atoms or a group represented by formula (IV) as described above, but $R^3$ is more preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV), and even more preferably a fluorine atom, a methyl group, an ethyl group, a methoxy group, an ethoxy group, or a group represented by formula (IV).

In a case in which $R^2$ in formula (I) is a group represented by formula (II), $R^3$ in formula (II) has the same preferable definition as $R^3$ in the case where $R^1$ in formula (I) is a group represented by formula (II).

A preferred combination of $R^1$ and $R^2$ in formula (I) is a combination in which $R^1$ represents a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III), and $R^2$ represents a hydrogen atom, an alkyl group having from 1 to 3 carbon atoms, a group represented by formula (II) (in formula (II), $R^3$ is preferably a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

A more preferred combination of $R^1$ and $R^2$ in formula (I) is a combination in which $R^1$ represents a group represented by formula (II) (in formula (II), $R^3$ is preferably a fluorine atom, a methyl group, an ethyl group, a methoxy group, an ethoxy group, or a group represented by formula (IV)), or a group represented by formula (III), and $R^2$ represents a hydrogen atom or a methyl group.

A particularly preferred combination of $R^1$ and $R^2$ in formula (I) is a combination in which in formula (I), $R^1$ represents a group represented by formula (III) and $R^2$ represents a hydrogen atom (most preferably 1,2:3,4-di-O-sulfanyl-meso-erythritol).

A cyclic sulfate compound in which $R^1$ in formula (I) is a group represented by formula (II), is a cyclic sulfate compound represented by the following formula (XII).

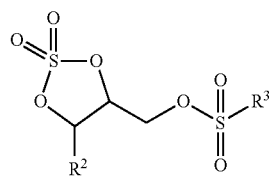

(XII)

In formula (XII), $R^2$ and $R^3$ have the same definitions as $R^2$ and $R^3$ in formula (I) and formula (II), respectively.

The cyclic sulfate compound represented by formula (XII) is preferably a compound in which $R^2$ represents a hydrogen atom or an alkyl group having from 1 to 6 carbon atoms, $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV).

Furthermore, the cyclic sulfate compound represented by formula (XII) is particularly preferably a compound in which $R^2$ represents a hydrogen atom or a methyl group, and $R^3$ represents a fluorine atom, a methyl group, an ethyl group, a methoxy group, an ethoxy group, or a group represented by formula (IV).

The cyclic sulfate compound represented by formula (I) is preferably 4-methylsulfonyloxymethyl-2,2-dioxo-1,3,2-dioxathiolane, 4-ethylsulfonyloxymethyl-2,2-dioxo-1,3,2-dioxathiolane, bis((2,2-dioxo-1,3,2-dioxathiolane-4-yl)methyl) sulfate, 1,2:3,4-di-O-sulfanyl-meso-erythritol, or 1,2:3,4-di-O-sulfanyl-D,L-threitol; more preferably 4-methylsulfonyloxymethyl-2,2-dioxo-1,3,2-dioxathiolane, 4-ethylsulfonyloxymethyl-2,2-dioxo-1,3,2-dioxathiolane, bis((2,2-dioxo-1,3,2-dioxathiolane-4-yl)methyl) sulfate, or 1,2:3,4-di-O-sulfanyl-meso-erythritol; and particularly preferably 4-methylsulfonyloxymethyl-2,2-dioxo-1,3,2-dioxathiolane, 4-ethylsulfonyloxymethyl-2,2-dioxo-1,3,2-dioxathiolane, or bis((2,2-dioxo-1,3,2-dioxathiolane-4-yl)methyl) sulfate.

Specific examples of the cyclic sulfate compound represented by formula (I) according to the invention [exemplary compound 1 to exemplary compound 30] will be described in the following table by specifying the respective substituents for formula (I), but the invention is not intended to be limited to these compounds.

In the structures of the exemplary compounds described below, "Me" represents a methyl group, "Et" represents an ethyl group, "Pr" represents a propyl group, "iPr" represents an isopropyl group, "Bu" represents a butyl group, "tBu" represents a tertiary butyl group, "Pent" represents a pentyl group, "Hex" represents a hexyl group, "OMe" represents a methoxy group, "OEt" represents an ethoxy group, "OPr" represents a propoxy group, "OBu" represents a butoxy group, "OPent" represents a pentyloxy group, "OHex" represents a hexyloxy group. Furthermore, the "wavy line" in $R^1$ to $R^3$ represents the position of bonding.

Meanwhile, a 2,2-dioxo-1,3,2-dioxathiolane ring may have stereoisomers arising from the substituents at the 4-position and the 5-position, but both the isomers are compounds that are included in the invention.

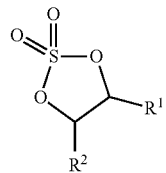

(I)

| Exemplary Compound No. | $R^1$ | $R^2$ | $R^3$ |
|---|---|---|---|
| 1 | ~O-S(=O)(=O)-R³ | H | Me |
| 2 | ~O-S(=O)(=O)-R³ | H | Et |
| 3 | ~O-S(=O)(=O)-R³ | H | Pr |
| 4 | ~O-S(=O)(=O)-R³ | H | iPr |

-continued
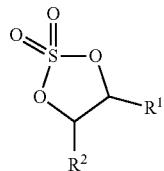
(I)
| Exemplary Compound No. | R¹ | R² | R³ |
|---|---|---|---|
| 5 | 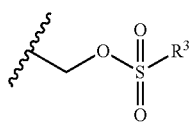 | H | Bu |
| 6 | 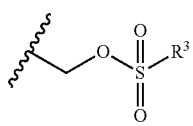 | H | tBu |
| 7 | 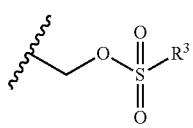 | H | Pent |
| 8 | 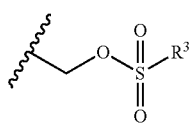 | H | Hex |
| 9 | 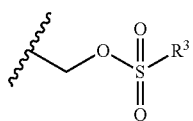 | H | $CF_3$ |
| 10 | 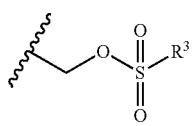 | H | $CHF_2$ |
| 11 | 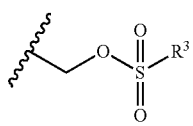 | H | $CH_2CF_3$ |
| 12 | 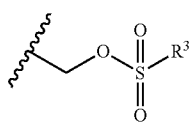 | H | $CH_2CH_2CF_3$ |
| 13 | 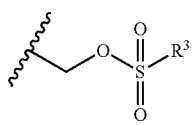 | H | $CH_2CH_2CH_2CF_3$ |
| 14 | 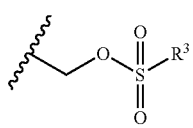 | H | $CH_2CH_2CH_2CH_2CF_3$ |

-continued
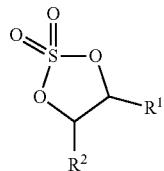
(I)
| Exemplary Compound No. | R¹ | R² | R³ |
|---|---|---|---|
| 15 | -CH₂CH₂-O-S(=O)₂-R³ | H | $CH_2CH_2CH_2CH_2CH_2CF_3$ |
| 16 | -CH₂CH₂-O-S(=O)₂-R³ | H | -CH₂-O-CH₂-(1,3,2-dioxathiolane 2,2-dioxide) |
| 17 | -CH₂CH₂-O-S(=O)₂-R³ | Me | Me |
| 18 | -CH₂CH₂-O-S(=O)₂-R³ | Et | Me |
| 19 | -CH₂CH₂-O-S(=O)₂-R³ | Hex | Me |
| 20 | -CH₂CH₂-O-S(=O)₂-R³ | -CH₂CH₂-O-S(=O)₂-R³ | Me |
| 21 | -CH₂CH₂-O-S(=O)₂-R³ | -CH₂CH₂-O-S(=O)₂-R³ | Et |
| 22 | (1,3,2-dioxathiolane 2,2-dioxide)-yl | H | — |
| 23 | (1,3,2-dioxathiolane 2,2-dioxide)-yl | (1,3,2-dioxathiolane 2,2-dioxide)-yl | — |

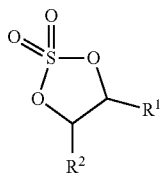

| Exemplary Compound No. | R¹ | R² | R³ |
|---|---|---|---|
| 24 | (CH₂-O-S(=O)₂-R³) | H | F |
| 25 | (CH₂-O-S(=O)₂-R³) | H | OMe |
| 26 | (CH₂-O-S(=O)₂-R³) | H | OEt |
| 27 | (CH₂-O-S(=O)₂-R³) | H | OPr |
| 28 | (CH₂-O-S(=O)₂-R³) | H | OBu |
| 29 | (CH₂-O-S(=O)₂-R³) | H | OPent |
| 30 | (CH₂-O-S(=O)₂-R³) | H | OHex |

Among the cyclic sulfate compounds represented by formula (I), in the case where two or more asymmetric carbon atoms are present in the molecule, the relevant compounds respectively have stereoisomers (diastereomers), but unless particularly stated otherwise, each of the relevant compounds is a mixture of corresponding diastereomers.

For example, exemplary compound 22 (4,4'-bis(2,2-dioxo-1,3,2-dioxathiolane) has two kinds of diastereomers, which are indicated as exemplary compound 22a described below and exemplary compound 22b described below, respectively.

In the present specification, the exemplary compound 22a may be referred to as 1,2:3,4-di-O-sulfanyl-meso-erythritol, and the exemplary compound 22b may be referred to as 1,2:3,4-di-O-sulfanyl-D,L-threitol.

Exemplary Compound 22a

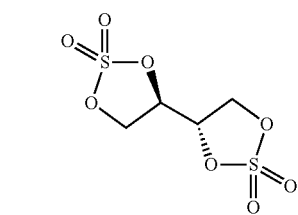

Exemplary Compound 22b

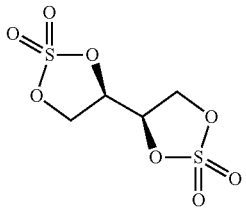

Meanwhile, the cyclic sulfate compound represented by formula (I) is useful as an additive for lithium secondary batteries as will be described below.

The cyclic sulfate compound represented by formula (I) in the invention, in which $R^1$ represents a group represented by formula (II) (for example, a cyclic sulfate compound represented by formula (XII)), can be produced by, for example, the process that will be described below, but the production method is not intended to be limited to this production method.

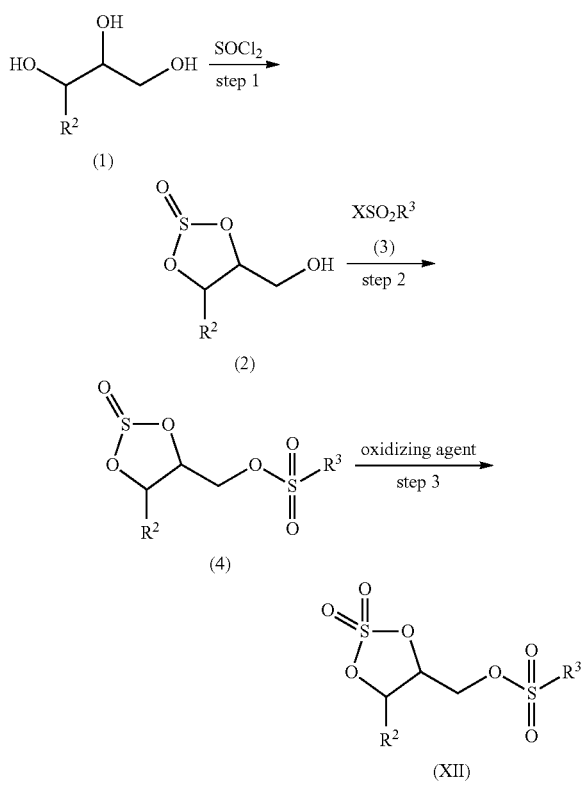

In the above formula, $R^2$ and $R^3$ have the same definitions as $R^2$ and $R^3$ in formula (I), respectively; and in the above formula, X represents a halogen atom.

(Step 1)

Step 1 is a step for producing a cyclic sulfurous acid ester represented by formula (2) (hereinafter, also referred to as "compound (2)") by causing an alcohol derivative represented by formula (I) (hereinafter, also referred to as "compound (1)") to react with thionyl chloride.

In regard to the present step, the solvent to be used is not particularly limited as long as the solvent does not inhibit the reaction and is capable of dissolving the starting materials to some extent, and examples thereof include ethers such as diethyl ether, dimethoxyethane, tetrahydrofuran, and dioxane; aromatic hydrocarbons such as benzene, toluene, xylene and chlorobenzene; aliphatic hydrocarbons such as hexane, cyclohexane and heptane; halogenated hydrocarbons such as methylene chloride, 1,2-dichloroethane and chloroform; and mixture thereof. Suitable solvents are halogenated hydrocarbons, aliphatic hydrocarbons, and aromatic hydrocarbons, and more suitable solvents are methylene chloride and toluene.

The amount of thionyl chloride to be used is 1.0 mol to 5.0 mol, and suitably 1.0 mol to 2.0, mol, relative to 1 mol of the compound (1).

Regarding the amount of the solvent, usually 0.3 liters to 5 liters, and suitably 0.5 liters to 2 liters, can be used relative to 1 mol of the compound (1).

The reaction temperature may vary depending on the raw material compounds, reaction reagents, solvents and the like, but usually, the reaction can be carried out in a temperature range of from $-20°$ C. to the reflux temperature in the reaction system, and suitably $-10°$ C. to $20°$ C.

The reaction time may vary depending on the raw material compounds, reaction reagents, solvents, reaction temperature, and the like, but usually, the reaction can be carried out in the range of 0.5 hours to 48 hours, and suitably 0.5 hours to 24 hours.

The compound (1) used in the present step may be a commercially available product, or is produced according to an already known method, for example, the method described in Tetrahedron: Asymmetry, 2005, Vol. 16, p. 3268-3274.

(Step 2)

Step 2 is a step for producing a cyclic sulfurous acid ester (4) represented by formula (4) (hereinafter, also referred to as "compound (4)") by causing the cyclic sulfurous acid ester represented by formula (2) (compound (2)) to react with a compound represented by formula (3) in the presence of a base.

In the present step, the base to be used is not particularly limited as long as it is a base exhibiting a deprotonation ability against the substrate, and examples thereof include carbonates of alkali metals, such as sodium carbonate and potassium carbonate; hydrogen carbonates of alkali metals, such as sodium hydrogen carbonate and potassium hydrogen carbonate; organic bases such as triethylamine, N,N-dimethylaniline, and pyridine; metal hydrides such as sodium hydride and potassium hydride; and metal alkoxides such as sodium methoxide, sodium ethoxide, and potassium tert-butoxide. Suitable bases are organic bases, and a more suitable base is triethylamine.

In the present step, the solvent to be used is not particularly limited as long as the solvent does not inhibit the reaction and is capable of dissolving the starting materials to some extent, and examples thereof include ethers such as diethyl ether, dimethoxyethane, tetrahydrofuran, and dioxane; aromatic hydrocarbons such as benzene, toluene, xylene, and chlorobenzene; aliphatic hydrocarbons such as hexane, cyclohexane, and heptane; halogenated hydrocarbons such as methylene chloride, 1,2-dichloroethane, and chloroform; esters such as ethyl acetate and butyl acetate; and mixture thereof. Suitable solvents include halogenated hydrocarbons, aliphatic hydrocarbons, and aromatic hydrocarbons, and more suitable solvents include methylene chloride and toluene.

The amount of the solvent that can be used is usually 0.5 liters to 10 liters, and suitably 1.0 liter to 5 liters, relative to 1 mol of the compound (2).

The reaction temperature may vary depending on the raw material compounds, reaction reagents, solvents and the like, but usually, the reaction can be carried out in a temperature range of from −20° C. to the reflux temperature in the reaction system, and suitably −10° C. to 50° C.

The reaction time may vary depending on the raw material compounds, reaction reagents, solvents, reaction temperature, and the like, but usually, the reaction can be carried out in the range of 0.5 hours to 48 hours, and suitably 0.5 hours to 24 hours.

(Step 3)

Step 3 is a step for producing a cyclic sulfate (XII) by causing the cyclic sulfurous acid ester derivative represented by formula (4) (compound (4)) to react with an oxidizing agent.

In the present step, examples of the oxidizing agent that may be used include ruthenium salts such as ruthenium oxide, ruthenium chloride, and ruthenium bromide, or hydrates thereof. Suitable oxidizing agents are ruthenium oxide and ruthenium trichloride hydrate. Examples of co-oxidizing agents for the present reaction system include sodium periodate, sodium perchlorate, sodium chlorite, and sodium hypochlorite, and suitable examples include sodium hypochlorite and sodium periodate.

In the present step, the solvent to be used is not particularly limited as long as the solvent does not inhibit the reaction and is capable of dissolving the starting materials to some extent, and examples thereof include water; ethers such as diethyl ether, dimethoxyethane, tetrahydrofuran, and dioxane; aromatic hydrocarbons such as benzene, toluene, xylene, and chlorobenzene; aliphatic hydrocarbons such as hexane, cyclohexane, and heptane; halogenated hydrocarbons such as methylene chloride, 1,2-dichloroethane, and chloroform; esters such as ethyl acetate and butyl acetate; nitriles such as acetonitrile and propionitrile; and mixture thereof. Suitable solvents include esters, nitriles, water, and mixture thereof, and a more suitable solvent is a mixture of acetonitrile and water.

The amount of the solvent that can be used is usually 0.5 liters to 10 liters, and suitably 1.0 liter to 5 liters, relative to 1 mol of the compound (4).

The reaction temperature may vary depending on the raw material compounds, reaction reagents, solvent and the like, but usually, the reaction can be carried out in a temperature range of from −20° C. to the reflux temperature in the reaction system, and suitably −10° C. to 50° C.

The reaction time may vary depending on the raw material compounds, reaction reagents, solvent, reaction temperature, and the like, but usually, the reaction can be carried out in the range of 0.5 hours to 48 hours, and suitably 0.5 hours to 24 hours.

The cyclic sulfate compound represented by formula (I) of the invention, in which $R^1$ represents a group represented by formula (III), can be produced by an already known method, for example, the method described in Tetrahedron Letters, 2000, vol. 41, p. 5053-5056.

The cyclic sulfate compound represented by formula (I) is useful as an additive for lithium secondary batteries, particularly as an additive for a non-aqueous electrolyte solution for lithium secondary batteries that will be described below. When this additive is added to a non-aqueous electrolyte solution, a decrease in the open circuit voltage during the storage of a battery in a charged state can be suppressed, while the capacity retention performance of the battery is improved.

Now, a speculated reason why the cyclic sulfate compound represented by formula (I) offers the above-described effects will be explained below.

As a result of the investigation conducted by the inventors of the invention, it was found that when a compound having a structure of a simple cyclic sulfate, which is a cyclic sulfate compound that is not included in formula (I), is used, the capacity retention performance of a battery is improved, but a decrease in the potential (a decrease in the open circuit voltage during the storage of the battery in a charged state) is brought about. In contrast to this, it was found that when a cyclic sulfate compound represented by formula (I) (a compound having a structure in which a sulfuric acid ester structure is further added to one cyclic sulfate structure) is used, a decrease in potential can be suppressed while the capacity retention performance of the battery is improved.

It is speculated that such an effect is obtained because at the time of forming a passivation film on the negative electrode side by initial charging, as the cyclic sulfate compound represented by formula (I) having the structure forms a passivation film more firmly on the negative electrode side, continuous solvent decomposition or the like at the electrode surface is suppressed.

However, the invention is not intended to be limited by the speculation as described above.

The cyclic sulfate compound represented by formula (I) that is included in the non-aqueous electrolyte solution of the invention may be used singly, or two or more kinds may be used.

The content (if two or more kinds are included, the total content) of the cyclic sulfate compound represented by formula (I) that is included in the non-aqueous electrolyte solution of the invention is preferably 0.001 mass % to 10 mass %, and more preferably in the range of 0.05 mass % to 5 mass %, relative to the total mass of the non-aqueous electrolyte solution. When the content is in this range, a decrease in the open circuit voltage during battery storage can be more effectively suppressed, while the capacity of the battery is retained.

[Electrolyte Compound Represented by Formula (V) and Lithium Difluorophosphate]

The non-aqueous electrolyte solution of the invention preferably further contains at least one of an electrolyte compound represented by the following formula (V) or lithium difluorophosphate ($LiOP(O)F_2$), in addition to the cyclic sulfate compound represented by formula (I) described above.

Thereby, a decrease in the open circuit voltage during the storage of a battery in a charged state can be suppressed, while the capacity retention performance of the battery is improved, and also, the low temperature discharge characteristics of the battery in the early stage and during storage in a charged state can be enhanced. That is, when the non-aqueous electrolyte solution of the invention contains the cyclic sulfate compound represented by formula (I) described above, and at least one of an electrolyte compound represented by the following formula (V) or lithium difluorophosphate ($LiOP(O)F_2$), a good balance can be achieved between the initial characteristics of a battery and the storage characteristics of the battery.

Here, if the non-aqueous electrolyte solution does not contain the cyclic sulfate compound represented by formula (I) described above but contains at least one of the electrolyte compound represented by the following formula (V) or lithium difluorophosphate ($LiOP(O)F_2$), the effect of enhancing the low temperature discharge characteristics of the battery in the early stage may be obtained, but the storage characteristics of the battery cannot be sufficiently satisfied. That is, in this case, the low temperature discharge characteristics during storage or the capacity retention performance during storage may deteriorate, and a decrease in the open circuit voltage during storage may not be suppressed.

Hereinafter, the electrolyte compound represented by formula (V) will be described.

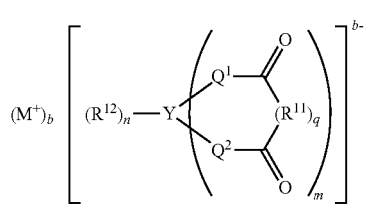

In formula (V), M represents an alkali metal; Y represents a transition element, or an element of Group 13, Group 14 or Group 15 of the Periodic Table of Elements; b represents an integer from 1 to 3; m represents an integer from 1 to 4; n represents an integer from 0 to 8; q represents 0 or 1; $R^{11}$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, wherein such groups may each contain a substituent or a heteroatom in the structure, and when q is 1 and m is 2 to 4, m units of $R^{11}$ may be bonded to each other; $R^{12}$ represents a halogen atom, an alkyl group having from 1 to 10 carbon atoms, a halogenated alkyl group having from 1 to 10 carbon atoms, an aryl group having from 6 to 20 carbon atoms, a halogenated aryl group having from 6 to 20 carbon atoms, or -$Q^3R^{13}$, wherein such groups, other than -$Q^3R^{13}$, may each contain a substituent or a heteroatom in the structure, and when n represents an integer from 2 to 8, n units of $R^{12}$ may be bonded to each other to form a ring; $Q^1$, $Q^2$, and $Q^3$ each independently represent O, S or $NR^{14}$; and $R^{13}$ and $R^{14}$ each independently represent a hydrogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, wherein such groups may each contain a substituent or a heteroatom in the structure, and when plural $R^{13}$'s or plural $R^{14}$'s are present, the respective groups may be bonded to each other to form a ring.

In the electrolyte compound represented by formula (V), M represents an alkali metal, and Y represents a transition metal or an element of Group 13, Group 14 or Group 15 of the Periodic Table of Elements. Among these, Y is preferably Al, B, V, Ti, Si, Zr, Ge, Sn, Cu, Y, Zn, Ga, Nb, Ta, Bi, P, As, Sc, Hf, or Sb, and more preferably Al, B or P. When Y represents Al, B or P, synthesis of the anion compound is made relatively easy, and the production cost can be lowered. Symbol b, which represents the valency of the anion and the number of cations, is an integer from 1 to 3, and is preferably 1. If b is greater than 3, there is a tendency that the salt of the anion compound does not easily dissolve in a mixed organic solvent, which is not preferable. Furthermore, the constants m and n are values related to the number of ligands and are determined in accordance with the kind of M; however, m represents an integer from 1 to 4, and n represents an integer from 0 to 8. The constant q is 0 or 1. When q is 0, the chelate ring becomes a 5-membered ring, and when q is 1, the chelate ring becomes a 6-membered ring.

$R^{11}$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms. These alkylene group, halogenated alkylene group, arylene group and halogenated arylene group may each contain a substituent or a heteroatom in the structure. Specifically, these groups may each contain a halogen atom, a chain-link or cyclic alkyl group, an aryl group, an alkenyl group, an alkoxy group, an aryloxy group, a sulfonyl group, an amino group, a cyano group, a carbonyl group, an acyl group, an amide group, or a hydroxyl group as a substituent, instead of a hydrogen atom. Furthermore, these groups may also have a structure in which a nitrogen atom, a sulfur atom or an oxygen atom is introduced instead of the carbon element. Also, when q is 1 and m is 2 to 4, m units of $R^{11}$ may be bonded to each other. An example thereof may be a ligand such as ethylenediamine tetraacetate.

$R^{12}$ represents a halogen atom, an alkyl group having from 1 to 10 carbon atoms, a halogenated alkyl group having from 1 to 10 carbon atoms, an aryl group having from 6 to 20 carbon atoms, a halogenated aryl group having from 6 to 20 carbon atoms, or -$Q^3R^{13}$ ($Q^3$ and $R^{13}$ will be explained below).

These alkyl group, halogenated alkyl group, aryl group and halogenated aryl group for $R^{12}$ may each contain a substituent or a heteroatom in the structure as in the case of $R^{11}$, and when n is 2 to 8, n units of $R^{12}$ may be bonded to each other to form a ring. $R^{12}$ is preferably an electron-withdrawing group, and is particularly preferably a fluorine atom.

$Q^1$, $Q^2$ and $Q^3$ each independently represent O, S or $NR^{14}$. That is, a ligand is bonded to Y through these heteroatoms.

$R^{13}$ and $R^{14}$ each independently represent a hydrogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms. These alkyl group, halogenated alkyl group, aryl group and halogenated aryl group may each contain a substituent or a heteroatom in the structure as in the case of $R^{11}$. Furthermore, when there are plural $R^{13}$'s or plural $R^{14}$'s, the respective groups may be bonded to each other to form a ring.

Examples of the alkali metal for M include lithium, sodium and potassium. Among these, lithium is particularly preferred.

n is preferably an integer from 0 to 4.

When the non-aqueous electrolyte solution of the invention includes an electrolyte compound represented by formula (V), the non-aqueous electrolyte solution of the invention may include only one kind of the compound represented by formula (V), or may include two or more kinds thereof.

Furthermore, the electrolyte compound represented by formula (V) is more preferably at least one compound selected from the group consisting of a compound represented by the following formula (VI), a compound represented by the following formula (VII), a compound represented by the following formula (VIII), and a compound represented by the following formula (IX). In regard to the compounds represented by formulas (VI) to (IX), a compound in which M represents lithium, sodium or potassium may be mentioned as a more preferred compound of the electrolyte compound represented by formula (V), and particularly preferably, the electrolyte compound is a compound represented by formula (VIII), in which M represents lithium.

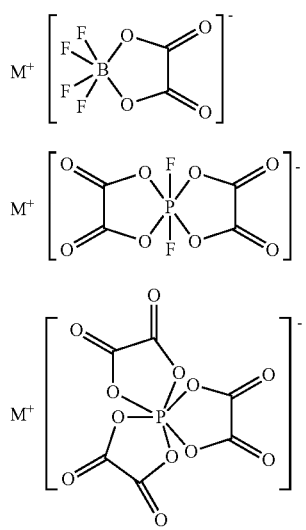

In formulas (VI) to (IX), M has the same definition as M in formula (V).

In regard to the method for synthesizing the electrolyte compound represented by formula (V), for example, in the case of a compound represented by formula (VI), a method of causing $LiBF_4$ to react with a lithium alkoxide in a two-fold molar amount of $LiBF_4$ in a non-aqueous solvent, subsequently adding oxalic acid, and substituting the alkoxide bonded to boron with oxalic acid, may be used.

Furthermore, in the case of a compound represented by formula (VII), a method of causing $LiPF_6$ to react with oxalic acid in a one-fold molar amount of this $LiPF_6$ in a non-aqueous solvent, and substituting the fluorine atom bonded to phosphorus with oxalic acid, may be used.

Furthermore, in the case of a compound represented by formula (VIII), a method of causing $LiPF_6$ to react with oxalic acid in a two-fold molar amount of this $LiPF_6$ in a non-aqueous solvent, and substituting the fluorine atom bonded to phosphorus with oxalic acid, may be used.

Also, in the case of a compound represented by formula (IX), a method of causing $LiPF_6$ to react with oxalic acid in a 3-fold molar amount of this $LiPF_6$ in a non-aqueous solvent, and substituting the fluorine atom bonded to phosphorus with oxalic acid, may be used.

In these cases, lithium salts of the anion compounds can be obtained.

When the non-aqueous electrolyte solution of the invention includes at least one of the electrolyte compound represented by formula (V) or lithium difluorophosphate, the content of at least one (if two or more kinds are included, the total content) of the electrolyte compound represented by formula (V) or lithium difluorophosphate is preferably 0.001 mass % to 10 mass %, and more preferably in the range of 0.05 mass % to 5 mass %, relative to the total mass of the non-aqueous electrolyte solution. When the content is in this range, a balance can be achieved more effectively between an improvement in the low temperature characteristics of a battery and an improvement in the storage characteristics of the battery.

Furthermore, when the non-aqueous electrolyte solution of the invention includes at least one of the electrolyte compound represented by formula (V) or lithium difluorophosphate, the content (if two or more kinds are included, the total content) of the cyclic sulfate compound represented by formula (I) is preferably 0.001 mass % to 10 mass %, and more preferably in the range of 0.05 mass % to 5 mass %, relative to the total mass of the non-aqueous electrolyte solution. When the content is in this range, a balance can be achieved more effectively between an improvement in the low temperature discharge characteristics of a battery and an improvement in the storage characteristics of the battery.

The non-aqueous electrolyte solution of the invention may also include other components in addition to the cyclic sulfate compound represented by formula (I) (and at least one of the electrolyte compound represented by formula (V) or lithium difluorophosphate that are used according to necessity). Regarding the other components, any known components can be optionally included.

The other components that are preferably included in the non-aqueous electrolyte solution of the invention will be explained. The non-aqueous electrolyte solution generally contains an electrolyte and a non-aqueous solvent.

Furthermore, an example of the other components that are preferably included in the non-aqueous electrolyte solution of the invention may be at last one compound represented by formula (X) shown below or formula (XI) shown below, from the viewpoint of obtaining the effects of the invention more effectively.

[Non-Aqueous Solvent]

Regarding the non-aqueous solvent related to the invention, various known solvents can be appropriately selected, but it is preferable to use a cyclic aprotic solvent and/or a linear aprotic solvent.

When an increase in the flash point of the solvent is intended to enhance the safety of the battery, it is preferable to use a cyclic aprotic solvent as the non-aqueous solvent.

[Cyclic Aprotic Solvent]

Examples of the cyclic aprotic solvent that can be used include a cyclic carbonate, a cyclic carboxylic acid ester, a cyclic sulfone, and a cyclic ether.

The cyclic aprotic solvent may be used alone, or a mixture of plural kinds may also be used.

The mixing proportion of the cyclic aprotic solvent in the non-aqueous solvent is 10 mass % to 100 mass %, more preferably 20 mass % to 90 mass %, and particularly preferably 30 mass % to 80 mass %. When such a ratio is employed, the conductivity of the electrolyte solution that is related to the charge-discharge characteristics of the battery can be increased.

Specific examples of the cyclic carbonate include ethylene carbonate, propylene carbonate, 1,2-butylene carbonate, 2,3-butylene carbonate, 1,2-pentylene carbonate, and 2,3-pentylene carbonate. Among these, ethylene carbonate and propylene carbonate having high dielectric constants are suitably used. In the case of a battery using graphite as the negative electrode active material, ethylene carbonate is more preferable. Also, two or more kinds of these cyclic carbonates may also be used in mixture.

Specific examples of the cyclic carboxylic acid ester include γ-butyrolactone, δ-valerolactone, and alkyl-substituted forms such as methyl-γ-butyrolactone, ethyl-γ-butyrolactone, and ethyl-δ-valerolactone.

A cyclic carboxylic acid ester has a low vapor pressure, has low viscosity, has a high dielectric constant, and can lower the viscosity of the electrolyte solution without decreasing the flash point of the electrolyte solution and the degree of dissociation of the electrolyte. For this reason, a cyclic carboxylic acid ester has a feature that the conductivity of the electrolyte solution, which is an index associated with the discharge characteristics of a battery, can be increased without increasing the inflammability of the electrolyte solution. Therefore, in the case where an improvement in the flash point of the solvent is intended, it is preferable to use a cyclic carboxylic acid ester as the cyclic aprotic solvent. Among cyclic carboxylic acid esters, γ-butyrolactone is most preferred.

Furthermore, it is preferable to use a cyclic carboxylic acid ester as a mixture with another cyclic aprotic solvent. For example, a mixture of a cyclic carboxylic acid ester and a cyclic carbonate and/or an acyclic carbonate may be used.

Examples of the cyclic sulfone include sulfolane, 2-methylsulfolane, 3-methylsulfolane, dimethylsulfone, diethylsulfone, dipropylsulfone, methylethylsulfone, and methylpropylsulfone.

Examples of the cyclic ether include dioxolane.

[Acyclic Aprotic Solvent]

Examples of the acyclic aprotic solvent of the invention that can be used include an acyclic carbonate, an acyclic carboxylic acid ester, an acyclic ether, and an acyclic phosphoric acid ester.

The mixing proportion of the acyclic aprotic solvent in the non-aqueous solvent is 10 mass % to 100 mass %, more preferably 20 mass % to 90 mass %, and particularly preferably 30 mass % to 80 mass %.

Specific examples of the acyclic carbonate include dimethyl carbonate, methyl ethyl carbonate, diethyl carbonate, methyl propyl carbonate, methyl isopropyl carbonate, ethyl propyl carbonate, dipropyl carbonate, methyl butyl carbonate, ethyl butyl carbonate, dibutyl carbonate, methyl pentyl carbonate, ethyl pentyl carbonate, dipentyl carbonate, methyl heptyl carbonate, ethyl heptyl carbonate, diheptyl carbonate, methyl hexyl carbonate, ethyl hexyl carbonate, dihexyl carbonate, methyl octyl carbonate, ethyl octyl carbonate, dioctyl carbonate, and methyl trifluoroethyl carbonate. These acyclic carbonates may also be used as mixtures of two or more kinds.

Specific examples of the acyclic carboxylic acid ester include methyl pivalate.

Specific examples of the acyclic ether include dimethoxyethane.

Specific examples of the acyclic phosphoric acid ester include trimethyl phosphate.

[Combination of Solvents]

The non-aqueous solvent used in the non-aqueous electrolyte solution related to the invention may be used singly or as a mixture of plural kinds. Furthermore, only cyclic aprotic solvents may be used singly or as a combination of plural kinds; only acyclic aprotic solvents may be used singly or as a combination of plural kinds; or mixtures of cyclic aprotic solvents and acyclic protic solvents may also be used. Particularly when an enhancement of the rate characteristics and the low temperature characteristics of the battery is intended, it is preferable to use a cyclic aprotic solvent and an acyclic aprotic solvent in combination as the non-aqueous solvent.

Furthermore, in view of the electrochemical stability of the electrolyte solution, it is most preferable to apply a cyclic carbonate as the cyclic aprotic solvent, and to apply an acyclic carbonate as the acyclic aprotic solvent. Furthermore, when a combination of a cyclic carboxylic acid ester and a cyclic carbonate and/or acyclic carbonate is used, the conductivity of the electrolyte solution related to the charge-discharge characteristics of the battery can be increased.

Specific examples of the combination of a cyclic carbonate and an acyclic carbonate include ethylene carbonate with dimethyl carbonate; ethylene carbonate with methyl ethyl carbonate; ethylene carbonate with diethyl carbonate; propylene carbonate with dimethyl carbonate; propylene carbonate with methyl ethyl carbonate; propylene carbonate with diethyl carbonate; ethylene carbonate with propylene carbonate and methyl ethyl carbonate; ethylene carbonate with propylene carbonate and diethyl carbonate; ethylene carbonate with dimethyl carbonate and methyl ethyl carbonate; ethylene carbonate with dimethyl carbonate and diethyl carbonate; ethylene carbonate with methyl ethyl carbonate and diethyl carbonate; ethylene carbonate with dimethyl carbonate, methyl ethyl carbonate and diethyl carbonate; ethylene carbonate with propylene carbonate, dimethyl carbonate and methyl ethyl carbonate; ethylene carbonate with propylene carbonate, dimethyl carbonate and diethyl carbonate; ethylene carbonate with propylene carbonate, methyl ethyl carbonate and diethyl carbonate; and ethylene carbonate with propylene carbonate, dimethyl carbonate, methyl ethyl carbonate and diethyl carbonate.

The mixing proportion of the cyclic carbonate and the acyclic carbonate is such that when expressed as a mass ratio, the ratio of cyclic carbonate:acyclic carbonate is 5:95 to 80:20, more preferably 10:90 to 70:30, and particularly preferably 15:85 to 55:45. When such ratios are employed, an increase in the viscosity of the electrolyte solution is suppressed, and the degree of dissociation of the electrolyte can be increased. Therefore, the conductivity of the electrolyte solution related to the charge-discharge characteristics of a battery can be increased. Furthermore, the solubility of the electrolyte can be further increased. Accordingly, since an electrolyte solution having excellent electrical conductivity at normal temperature or at a low temperature can be obtained, the rate characteristics of a battery at normal temperature to a low temperature can be improved.

Specific examples of the combination of a cyclic carboxylic acid ester with a cyclic carbonate and/or an acyclic carbonate include γ-butyrolactone with ethylene carbonate; γ-butyrolactone with ethylene carbonate and dimethyl carbonate; γ-butyrolactone with ethylene carbonate and methyl ethyl carbonate; γ-butyrolactone with ethylene carbonate and diethyl carbonate; γ-butyrolactone with propylene carbonate; γ-butyrolactone with propylene carbonate and dimethyl carbonate; γ-butyrolactone with propylene carbonate and methyl ethyl carbonate; γ-butyrolactone with propylene carbonate and diethyl carbonate; γ-butyrolactone with ethylene carbonate and propylene carbonate; γ-butyrolactone with ethylene carbonate, propylene carbonate and dimethyl carbonate; γ-butyrolactone with ethylene carbonate, propylene carbonate and methyl ethyl carbonate; γ-butyrolactone with ethylene carbonate, propylene carbonate and diethyl carbonate; γ-butyrolactone with ethylene carbonate, dimethyl carbonate and methyl ethyl carbonate; γ-butyrolactone with ethylene carbonate, dimethyl carbonate and diethyl carbonate; γ-butyrolactone with ethylene carbonate, methyl ethyl carbonate and diethyl carbonate; γ-butyrolactone with ethylene carbonate, dimethyl carbonate, methyl ethyl carbonate, and diethyl carbonate; γ-butyrolactone with ethylene carbonate, propylene carbonate, dimethyl carbonate and methyl ethyl carbonate; γ-butyrolactone with ethylene carbonate, propylene carbonate, dimethyl carbonate and diethyl carbonate; γ-butyrolactone with ethylene carbonate, propylene carbonate, methyl ethyl carbonate, and diethyl carbonate; γ-butyrolactone with ethylene carbonate, propylene carbonate, dimethyl carbonate, methyl ethyl carbonate, and diethyl carbonate; γ-butyrolactone with sulfolane; γ-butyrolactone with ethylene carbonate and sulfolane; γ-butyrolactone with propylene carbonate and sulfolane; γ-butyrolactone with ethylene carbonate, propylene carbonate and sulfolane; and γ-butyrolactone with sulfolane and dimethyl carbonate.

[Other Solvent]

The non-aqueous electrolyte solution related to the invention may also include another solvent in addition to the solvents described above, as the non-aqueous solvent. Specific examples of the other solvent include amides such as dimethylformamide; acyclic carbamates such as methyl-N,N-diethyl carbamate; cyclic amides such as N-methylpyrrolidone; cyclic ureas such as N,N-dimethylimidazolidinone; boron compounds such as trimethyl borate, triethyl borate, tributyl borate, trioctyl borate, and trimethylsilyl borate; and polyethylene glycol derivatives represented by the following formulas:

HO(CH$_2$CH$_2$O)$_a$H

HO[CH$_2$CH(CH$_3$)O]$_b$H

CH$_3$O(CH$_2$CH$_2$O)$_c$H

CH$_3$O[CH$_2$CH(CH$_3$)O]$_d$H

CH$_3$O(CH$_2$CH$_2$O)$_e$CH$_3$

CH$_3$O[CH$_2$CH(CH$_3$)O]$_f$CH$_3$

C$_9$H$_{19}$PhO(CH$_2$CH$_2$O)$_g$[CH(CH$_3$)O]$_h$CH$_3$ (Ph represents a phenyl group)

CH$_3$O[CH$_2$CH(CH$_3$)O]$_i$CO[OCH(CH$_3$)CH$_2$]$_j$OCH$_3$

In the above formulas, a to f each represent an integer from 5 to 250; g to j each represent an integer from 2 to 249; 5≤g+h≤250; and 5≤i+j≤250.

[Compound Represented by Formula (X)]

The non-aqueous electrolyte solution of the invention may contain a compound represented by formula (X). An embodiment that the non-aqueous electrolyte solution of the invention contains a compound represented by formula (X) is preferable from the viewpoint of forming a passivation film of the negative electrode surface.

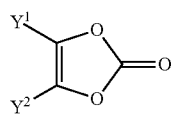

(X)

In formula (X), Y$^1$ and Y$^2$ each independently represent a hydrogen atom, a methyl group, an ethyl group, or a propyl group.

Examples of the compound represented by formula (X) include vinylene carbonate, methylvinylene carbonate, ethylvinylene carbonate, propylvinylene carbonate, dimethylvinylene carbonate, diethylvinylene carbonate, and dipropylvinylene carbonate. Among these, vinylene carbonate is most preferred.

When the non-aqueous electrolyte solution of the invention contains the compound represented by formula (X), the non-aqueous electrolyte solution of the invention may contain only one kind of the compound represented by formula (X), or may contain two or more kinds thereof.

The content (if two or more kinds are included, the total content) of the compound represented by formula (X) can be appropriately selected in accordance with the purpose, but the content is preferably 0.001 mass % to 10 mass %, and more preferably 0.05 mass % to 5 mass %, relative to the total mass of the non-aqueous electrolyte solution.

[Compound Represented by Formula (XI)]

The non-aqueous electrolyte solution related to the invention may contain a compound represented by formula (XI). An embodiment that the non-aqueous electrolyte solution of the invention contains a compound represented by formula (XI) is preferable from the viewpoint of forming a passivation film of the negative electrode surface.

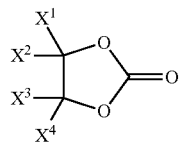

(XI)

In formula (XI), X$^1$, X$^2$, X$^3$ and X$^4$ each independently represent a hydrogen atom, a fluorine atom, a chlorine atom, or an alkyl group having from 1 to 3 carbon atoms which may be substituted with a fluorine atom, provided that X$^1$ to X$^4$ are not both hydrogen atoms at the same time.

In formula (XI), examples of the alkyl group having from 1 to 3 carbon atoms which may be substituted with a fluorine atom as represented by X$^1$ to X$^4$ include fluoromethyl, difluoromethyl, trifluoromethyl, pentafluoroethyl, and heptafluoropropyl.

Regarding the compound represented by formula (XI), known compounds can be used, and examples thereof include fluorinated ethylene carbonates in which 1 to 4 hydrogen atoms of ethylene carbonate are substituted by fluorine atoms, such as 4-fluoroethylene carbonate, 4,4-difluoroethylene carbonate, 4,5-difluoroethylene carbonate, 4,4,5-trifluoroethylene carbonate, and 4,4,5,5-tetrafluoroethylene carbonate. Among these, 4,5-difluoroethylene carbonate and 4-fluoroethylene carbonate are most preferred.

When the non-aqueous electrolyte solution of the invention contains the compound represented by the formula (XI), the non-aqueous electrolyte solution of the invention may contain only one kind of the compound represented by formula (XI), or may contain two or more kinds thereof.

The content (if two or more kinds are included, the total content) of the compound represented by formula (XI) can be appropriately selected in accordance with the purpose, but the content is preferably 0.001 mass % to 10 mass %, and more preferably 0.05 mass % to 5 mass %, relative to the total mass of the non-aqueous electrolyte solution.

[Electrolyte]

In the non-aqueous electrolyte solution of the invention, various electrolytes can be used, and usually, any electrolyte which is used as an electrolyte for non-aqueous electrolyte solutions can be used.

Regarding the electrolyte for the non-aqueous electrolyte solution of the invention, at least one of the electrolyte compound represented by formula (V) or lithium difluorophosphate may be used; another electrolyte having a structure that is different from the structures of the electrolyte compound represented by formula (V) or lithium difluorophosphate (hereinafter, also simply referred to as "other electrolyte") may be used; or at least one of the electrolyte compound represented by formula (V) or lithium difluorophosphate and another electrolyte may be used in combination.

Particularly, when the non-aqueous electrolyte solution of the invention contains at least one of the electrolyte compound represented by formula (V) or lithium difluorophosphate and another electrolyte, electrical conductivity which is a fundamental performance of an electrolyte for conventional non-aqueous electrolyte solutions is retained, and also, the battery performance (particularly, the low temperature discharge characteristics of the battery in the early stage and during storage in a charged state) is also further enhanced. Furthermore, when at least one of the electrolyte compound represented by formula (V), lithium difluorophosphate, or the other electrolyte contains lithium ions, the relevant compound serves as a stable supply source of lithium ions.

Specific examples of the other electrolyte include tetraalkylammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (k=an integer from 1 to 8), and $(C_2H_5)_4NPF_n[C_kF_{(2k+1)}]_{(6-n)}$ (n=an integer from 1 to 5, and k=an integer from 1 to 8); and lithium salts such as $LiPF_6$, $LiBF_4$, $LiClO_4$, $LiAsF_6$, $Li_2SiF_6$, $LiOSO_2C_kF_{(2k+1)}$ (k=an integer from 1 to 8), and $LiPF_n[C_kF_{(2k+1)}]_{(6-n)}$ (n=an integer from 1 to 5, and k=an integer from 1 to 8). Furthermore, lithium salts represented by the following formula can also be used:

$LiC(SO_2R^7)(SO_2R^8)(SO_2R^9)$, $LiN(SO_2OR^{10})(SO_2OR^{11})$, and $LiN(SO_2R^{12})(SO_2R^{13})$ (wherein $R^7$ to $R^{13}$ may be identical with or different from each other, and each represent a perfluoroalkyl group having from 1 to 8 carbon atoms). These electrolytes may be used singly, or two or more kinds may be used as mixtures.

Among these, lithium salts in particular are preferred, and $LiPF_6$, $LiBF_4$, $LiOSO_2C_kF_{(2k+1)}$ (k=an integer from 1 to 8), $LiClO_4$, $LiAsF_6$, $LiNSO_2[C_kF_{(2k+1)}]_2$ (k=an integer from 1 to 8), and $LiPF_n[C_kF_{(2k+1)}]_{(6-n)}$ (n=an integer from 1 to 5, and k=an integer from 1 to 8) are preferred.

An electrolyte is generally preferably included in the non-aqueous electrolyte at a concentration of 0.1 mol/L to 3 mol/L, and preferably 0.5 mol/L to 2 mol/L.

In regard to the non-aqueous electrolyte solution of the invention, in the case of using a cyclic carboxylic acid ester such as γ-butyrolactone in combination as the non-aqueous solvent, the non-aqueous electrolyte solution preferably contains $LiPF_6$ in particular. Since $LiPF_6$ has a high degree of dissociation, $LiPF_6$ can increase the conductivity of the electrolyte solution, and also has an action of suppressing the reductive decomposition reaction of the electrolyte solution on the negative electrode. $LiPF_6$ may be used alone, or $LiPF_6$ and another electrolyte may be used together. Regarding the other electrolyte, any electrolytes that are conventionally used as electrolytes for non-aqueous electrolyte solutions can all be used; however, among the specific examples of lithium salts described above, a lithium salt other than $LiPF_6$ is preferred.

Specific examples thereof include $LiPF_6$ with $LiBF_4$, $LiPF_6$ with $LiN[SO_2C_kF_{(2k+1)}]_2$ (k=an integer from 1 to 8), $LiPF_6$ with $LiBF_4$ and $LiN[SO_2C_kF_{(2k+1)}]$ (k=an integer from 1 to 8).

The proportion of $LiPF_6$ included in the lithium salts is preferably 1 mass % to 100 mass %, preferably 10 mass % to 100 mass %, and more preferably 50 mass % to 100 mass %. Such an electrolyte is preferably included in the non-aqueous electrolyte solution at a concentration of 0.1 mol/L to 3 mol/L, and preferably 0.5 mol/L to 2 mol/L.

The non-aqueous electrolyte solution of the invention is not only suitable as a non-aqueous electrolyte solution for lithium secondary batteries, but can also be used as a non-aqueous electrolyte solution for primary batteries, a non-aqueous electrolyte solution for electrochemical capacitors, or an electrolyte solution for electric double layer capacitors or aluminum electrolytic capacitors.

<Lithium Secondary Battery>

The lithium secondary battery of the invention is constituted to basically include a negative electrode, a positive electrode, and the non-aqueous electrolyte solution of the invention, and usually, a separator is provided between the negative electrode and the positive electrode.

(Negative Electrode)

As the negative electrode active material that constitutes the negative electrode, at least one selected from metal lithium, a lithium-containing alloy, a metal or alloy capable of alloying with lithium, an oxide capable of doping and dedoping of lithium ions, transition metal nitrides capable of doping and dedoping of lithium ions, and a carbon material capable of doping and dedoping of lithium ions (these may be used singly, or mixtures including two or more kinds of these may also be used) can be used.

Examples of the metal or alloy capable of alloying with lithium (or lithium ions) include silicon, a silicon alloy, tin, and a tin alloy. Furthermore, lithium titanate is also acceptable.

Among these, a carbon material capable of doping and dedoping of lithium ions is preferred. Examples of such a carbon material include carbon black, activated carbon, a graphite material (artificial graphite or natural graphite), and an amorphous carbon material. The form of the carbon material may be any of a fibrous form, a spherical form, a potato form and a flake form.

Specific examples of the amorphous carbon material include hard carbon, cokes, mesocarbon microbeads (MCMB) calcined at or below 1500° C., and mesophase pitch carbon fibers (MCF).

Examples of the graphite material include natural graphite and artificial graphite. Regarding the artificial graphite, graphitized MCMB, graphitized MCF, and the like are used. Furthermore, compounds containing boron can also be used as the graphite material. Also, as the graphite material, a graphite material coated with a metal such as gold, platinum, silver, copper or tin; a graphite material coated with an amorphous carbon; or a mixture of amorphous carbon and graphite can also be used.

These carbon materials may be used singly, or two or more kinds may also be used as mixtures.

The carbon material is particularly preferably a carbon material in which the interplanar spacing d(002) of the (002) plane measured by an X-ray analysis is 0.340 nm or less. Furthermore, the carbon material is also preferably a graphite having a true density of 1.70 g/cm$^3$ or greater, or a highly crystalline carbon material having properties close thereto. When a carbon material such as described above is used, the energy density of the battery can be further increased.

(Positive Electrode)

Examples of the positive electrode active material that constitutes the positive electrode include transition metal oxides or transition metal sulfides, such as $MoS_2$, $TiS_2$, $MnO_2$, and $V_2O_5$; composite oxides composed of lithium and transition metals, such as $LiCoO_2$, $LiMnO_2$, $LiMn_2O_4$, $LiNiO_2$, $LiNi_xCo_{(1-X)}O_2$ [$0<X<1$], and $LiFePO_4$; and electroconductive polymer materials such as polyaniline, polythiophene, polypyrrole, polyacetylene, polyacene, dimercaptothiadiazole, and a polyaniline composite. Among these, composite oxides composed of lithium and transition metals are particularly preferred. When the negative electrode is formed of lithium metal or a lithium alloy, a carbon material can be used as the positive electrode. Also, a mixture of a composite oxide of lithium and a transition metal with a carbon material can be used as the positive electrode.

The positive electrode active materials described above may be used singly, or two or more kinds may also be used as mixtures. If the positive electrode active material has insufficient electroconductivity, the positive electrode can be constructed by using the positive electrode active material together with an electroconductive aid. Examples of the electroconductive aid include carbon materials such as carbon black, amorphous whiskers, and graphite.

(Separator)

The separator is a membrane which electrically insulates the positive electrode and the negative electrode, and transmits lithium ions, and examples thereof include a porous film and a polymer electrolyte.

As the porous film, a finely porous polymer film is suitably used, and examples of materials of the porous film include polyolefins, polyimides, polyvinylidene fluoride, and polyesters.

Particularly, porous polyolefins are preferred, and specific examples thereof include a porous polyethylene film, a porous polypropylene film, and a multilayer film of a porous polyethylene film and a porous polypropylene film. A porous polyolefin film may also have another resin with excellent thermal stability coated thereon.

Examples of the polymer electrolyte include a polymer having a lithium salt dissolved therein, and a polymer swollen with an electrolyte solution.

The non-aqueous electrolyte solution of the invention may also be used for the purpose of obtaining a polymer electrolyte by swelling a polymer.

(Configuration of Battery)

The lithium secondary battery of the invention includes the negative electrode active material, positive electrode active material, and separator described above.

The lithium secondary battery of the invention can adopt various known shapes, and the lithium secondary battery can be formed into a cylindrical shape, a coin shape, a rectangular shape, a film shape, and any other shapes. However, the basic structure of the battery is the same irrespective of the shape, and modifications in design can be applied in accordance with the purpose.

An example of the non-aqueous electrolyte secondary battery of the invention may be a coin cell as illustrated in FIG. 1.

In the coin cell illustrated in FIG. 1, a disc-shaped negative electrode 2, a separator 5 in which a non-aqueous electrolyte solution obtained by dissolving an electrolyte in a non-aqueous solvent has been injected, a disc-shaped positive electrode 1, and optionally, spacer plates 7 and 8 made of stainless steel, aluminum or the like, which are laminated in this order, are accommodated between a positive electrode can 3 (hereinafter, also referred to as a "battery can") and a sealing plate 4 (hereinafter, also referred to as a "battery can lid"). The positive electrode can 3 and the sealing plate 4 are sealed by caulking with a gasket 6.

Meanwhile, the lithium secondary battery of the invention may be a lithium secondary battery obtained by charging and discharging a lithium secondary battery (a lithium secondary battery before being charged and discharged) which includes a negative electrode, a positive electrode, and the non-aqueous electrolyte solution of the invention.

That is, the lithium secondary battery of the invention may be a lithium secondary battery (a lithium secondary battery that has been charged and discharged) obtained by first producing a lithium secondary battery before being charged and discharged, which includes a negative electrode, a positive electrode and the non-aqueous electrolyte solution of the invention, and subsequently charging and discharging one or more times the lithium secondary battery before being charged and discharged.

There are no particular limitations on the use of the non-aqueous electrolyte solution of the embodiments of the invention, and of a lithium secondary battery using the non-aqueous electrolyte solution, and the electrolyte solution and the secondary battery can be used in various known applications. For example, the electrolyte solution and the secondary battery can be widely utilized in small-sized portable devices as well as in large-sized devices, such as notebook computers, mobile computers, mobile telephones, headphone stereos, video movie cameras, liquid crystal television sets, handy cleaners, electronic organizers, calculators, radios, back-up power supply applications, motors, automobiles, electric cars, motorcycles, electric motorcycles, bicycles, electric bicycles, illuminating devices, game players, time pieces, electric tools, and cameras.

EXAMPLES

Hereinafter, the present invention will be more specifically described by way of Examples, but the invention is not intended to be limited to these Examples. Meanwhile, in the following Examples, the unit "%" indicates mass %.

Hereinafter, Synthesis Examples of cyclic sulfate compounds represented by formula (I) will be described.

Synthesis Example 1

Synthesis of 4-methylsulfonyloxymethyl-2,2-dioxo-1,3,2-dioxathiolane (exemplary compound 1)

(Step 1)

47.0 g (85% yield) of 4-hydroxymethyl-2-oxo-1,3,2-dioxathiolane was obtained from glycerol (36.8 g) and thionyl chloride (47.6 g) according to the method described in Tetrahedron: Asymmetry, 1999, vol. 10 (24), p. 4755-4762.

(Step 2)

4-Hydroxymethyl-2-oxo-1,3,2-dioxathiolane (6.91 g, 50.0 mol) thus obtained was dissolved in tetrahydrofuran (140 ml), and under ice cooling, triethylamine (13.9 ml, 100 mmol) and methanesulfonyl chloride (4.3 ml, 55 mmol) were added thereto. The mixture was stirred for 3 hours. Water was poured into the reaction mixture, and the mixture was extracted with ethyl acetate. The extract was washed with a dilute aqueous hydrochloric acid solution and saturated brine, subsequently dried over anhydrous magnesium sulfate, and concentrated. The residue was purified by silica gel chromatography (elution solvent: hexane/ethyl acetate=2/3), and thus 4-methylsulfonyloxymethyl-2-oxo-1,3,2-dioxathiolane (9.47 g, 88% yield) was obtained.

The NMR analysis results for the compound were as follows.

$^1$H-NMR (270 MHz, CDCl$_3$) δ(ppm): 5.23-5.16 (0.6H, m), 4.85-4.79 (1.0H, m), 4.64-4.31 (3.4H, m), 3.11 (1.2H,$), 3.09 (1.8H,$)

(Step 3)

Sodium periodate (11.2 g, 52.3 mmol) and ruthenium trichloride (0.45 g, 2.2 mmol) were added to a mixture of acetonitrile (90 ml) and water (10 ml), and an acetonitrile solution (20 ml) of 4-methylsulfonyloxymethyl-2-oxo-1,3,2-dioxathiolane (9.42 g, 43.6 mmol) was added dropwise thereto at room temperature. The mixture was stirred for 3 hours at room temperature, subsequently 2-propanol (1 ml) was added to the reaction mixture, and the resulting mixture was stirred for one hour. The reaction mixture was diluted with ethyl acetate (300 ml), subsequently dried over anhydrous magnesium sulfate, and concentrated. The residue was purified by silica gel chromatography (elution solvent: hexane/ethyl acetate=1/1), and thus an exemplary compound 1 (5.96 g, 59% yield) was obtained.

The NMR analysis results for the exemplary compound 1 were as follows.

$^1$H-NMR (270 MHz, CDCl$_3$) δ(ppm): 5.23-5.15 (1H, m), 4.83 (1H, dd, J=9.3, 6.9), 4.66 (1H, dd, J=9.3, 5.9), 4.57 (1H, dd, J=12.5, 4.3), 4.47 (1H, dd, J=12.5, 4.6), 3.15 (3H, s).

Synthesis Example 2

Synthesis of 4-ethylsulfonyloxymethyl-2,2-dioxo-1,3,2-dioxathiolane (exemplary compound 2)

The same operation as that carried out for the synthesis of the exemplary compound 1 was carried out, except that in the Step 2 for the synthesis of the exemplary compound 1, methanesulfonyl chloride was changed to ethanesulfonyl chloride, and thus an exemplary compound 2 (3.37 g, 63% yield) was obtained.

The NMR analysis results for the exemplary compound 2 were as follows.

$^1$H-NMR (270 MHz, CDCl$_3$) δ(ppm): 5.23-5.16 (1H, m), 4.83 (1H, dd, J=9.2, 6.6), 4.65 (1H, J=9.2, 5.9), 4.52 (1H, dd, J=12.5, 4.0), 4.47 (1H, dd, J=12.5, 4.0), 3.26 (2H, q, J=7.6), 1.48 (3H, t, J=7.6)

Synthesis Example 3

Synthesis of bis((2,2-dioxo-1,3,2-dioxathiolane-4-yl)methyl) sulfate (exemplary compound 16)

(Step 1)
The same operation as that carried out in Step 1 for the synthesis of the exemplary compound 1 was carried out, and thus 4-hydroxymethyl-2-oxo-1,3,2-dioxathiolane was obtained.

(Step 2)
4-Hydroxymethyl-2-oxo-1,3,2-dioxathiolane (2.40 g, 17.4 mol) obtained in Step 1 was dissolved in methylene chloride (50 ml), and under ice cooling, triethylamine (3.6 ml, 26 mmol) and thionyl chloride (0.89 ml, 8.7 mmol) were added thereto. The mixture was stirred for 18 hours. Water was poured into the reaction mixture, and the mixture was extracted with methylene chloride. The extract was washed with a dilute aqueous hydrochloric acid solution and saturated brine, subsequently dried over anhydrous magnesium sulfate, and concentrated. The residue was purified by silica gel chromatography (elution solvent: hexane/ethyl acetate system), and thus bis((2-oxo-1,3,2-dioxathiolan-4-yl)methyl) sulfate (2.33 g, 83% yield) was obtained.

The NMR analysis results for the compound were as follows.

$^1$H-NMR (270 MHz, CDCl$_3$) δ(ppm): 5.17-5.12 (1.2H, m), 4.83-4.74 (2H, m), 4.62-4.58 (1.4H, m), 4.45-4.30 (2.7H, m), 4.26-4.03 (2.6H, m).

(Step 3)
Sodium periodate (5.26 g, 24.6 mmol) and ruthenium trichloride (0.15 g, 0.72 mmol) were added to a mixture of acetonitrile (45 ml) and water (5 ml), and an acetonitrile solution (4 ml) of bis((2-oxo-1,3,2-dioxathiolan-4-yl)methyl) sulfate (2.33 g, 7.23 mmol) was added dropwise thereto at room temperature. The mixture was stirred for 3 hours at room temperature, subsequently 2-propanol (3 ml) was added to the reaction mixture, and the resulting mixture was stirred for one hour. The reaction mixture was diluted with ethyl acetate (100 ml), subsequently dried over anhydrous magnesium sulfate, and concentrated.

The residue was purified by silica gel chromatography (elution solvent: hexane/ethyl acetate=1/1), and thus an exemplary compound 16 (1.88 g, 77% yield) was obtained.

The NMR analysis results for the exemplary compound 16 were as follows.

$^1$H-NMR (270 MHz, CDCl$_3$) δ(ppm): 5.66-5.58 (2H, m), 5.10 (2H, dd, J=9.5, 7.2), 4.93-4.86 (4H, m), 4.81-4.75 (2H, m).

Synthesis Example 4

Synthesis of 1,2:3,4-di-O-sulfanyl-meso-erythritol (exemplary compound 22a)

(Step 1)
10.53 g (98% yield) of di-O-sulfinyl-meso-erythritol was obtained from meso-erythritol (6.11 g) and thionyl chloride (14.88 g) according to the method of Step 1 of Synthesis Example 1.

(Step 2)
Sodium periodate (69.50 g, 325 mmol) and ruthenium trichloride (2.72 g, 13.1 mmol) were added to a mixture of acetonitrile (580 ml) and water (70 ml), and an acetonitrile solution (100 ml) of di-O-sulfinyl-meso-erythritol (28.0 g, 130.9 mmol) obtained as described above was added dropwise thereto at room temperature. The mixture was stirred for 3 hours at room temperature, subsequently 2-propanol (10 ml) was added to the reaction mixture, and the resulting mixture was stirred for one hour. The reaction mixture was diluted with ethyl acetate (500 ml), subsequently dried over anhydrous magnesium sulfate, and concentrated. The residue was purified by silica gel chromatography (elution solvent: hexane/ethyl acetate=1/1), and then crystals thus obtained were washed with ethyl acetate (100 ml). The mixture was filtered and then dried under reduced pressure, and thus an exemplary compound 22a (8.47 g, 26% yield) was obtained.

The NMR analysis results for the exemplary compound 22a were as follows.

$^1$H-NMR (270 MHz, acetone-d$_6$) δ(ppm): 5.76-5.69 (1H, m), 5.26-5.18 (1H, m), 5.10-5.00 (1H, m).

Synthesis Example 5

Synthesis of 1,2:3,4-di-O-sulfanyl-D,L-threitol (exemplary compound 22b)

(Step 1)
Imidazole (43.2 g, 635 mmol) was dissolved in tetrahydrofuran (100 ml), and under ice cooling, thionyl chloride (23.5 g, 199 mmol) was added thereto. The reaction mixture was stirred for 3 hours at room temperature, and then the salt thus produced was separated by filtration. Thus, a sulfinyldiimidazole solution was obtained.

In a separate flask, the sulfinyldiimidazole solution obtained as described above was added dropwise, under ice cooling, to a mixture of DL-threitol (10.0 g, 79.4 mmol) and tetrahydrofuran (50 ml). The temperature was raised to room temperature, and the mixture was stirred for 3 hours. The reaction mixture was poured into water, and the mixture was extracted with ethyl acetate. The extract was washed with a dilute aqueous hydrochloric acid solution and saturated brine, and was dried over anhydrous magnesium sulfate. The solution was concentrated, and 17.56 g of di-O-sulfinyl-D,L-threitol was obtained as a crude product.

(Step 2)
Sodium periodate (40.76 g, 190 mmol) and ruthenium trichloride (1.65 g, 7.9 mmol) were added to a mixture of acetonitrile (170 ml) and water (17 ml), and an acetonitrile solution (35 ml) of di-O-sulfinyl-D,L-threitol (17.56 g, 79.4 mmol) obtained as described above was added dropwise thereto at room temperature. The mixture was stirred for 3 hours at room temperature, subsequently 2-propanol (10 ml) was added to the reaction mixture, and the resulting mixture was stirred for one hour. The reaction mixture was diluted with ethyl acetate (200 ml), subsequently dried over anhydrous magnesium sulfate, and concentrated. The residue was purified by silica gel chromatography (elution solvent: hexane/ethyl acetate=1/1), and then crystals thus obtained were washed with ethyl acetate (50 ml). The mixture was filtered and then dried under reduced pressure, and thus an exemplary compound 22b (6.55 g, 34% yield) was obtained.

The NMR analysis results for the exemplary compound 22b were as follows.

$^1$H-NMR (270 MHz, acetone-$d_6$) δ(ppm): 5.72-5.65 (1H, m), 5.22-5.14 (1H, m), 5.04-4.96 (1H, m).

Thus, synthesis examples for the exemplary compound 1, exemplary compound 2, exemplary compound 16, exemplary compound 22a and exemplary compound 22b have been described as the synthesis examples for the cyclic sulfate compounds represented by formula (I). However, other cyclic sulfate compounds represented by formula (I) can also be synthesized by the same methods as those used in the Synthesis Examples described above.

Example 1-1

A lithium secondary battery was prepared by the following procedure.

Preparation of Negative Electrode 20 parts by mass of artificial graphite, 80 parts by mass of natural graphite-based graphite, 1 part by mass of carboxymethyl cellulose, and 2 parts by mass of a SBR latex were kneaded in water solvent, and thus a negative electrode mixture slurry in a paste form was prepared.

Next, this negative electrode mixture slurry was applied on a strip-shaped negative electrode current collector made of a copper foil having a thickness of 18 μm, and the slurry was dried. Subsequently, the assembly was compressed with a roll press, and thus a sheet-like negative electrode composed of a negative electrode current collector and a negative electrode active material layer was obtained. The coating density of the negative electrode active material layer in this case was 10 mg/cm$^2$, and the packing density was 1.5 g/ml.

Preparation of Positive Electrode 90 parts by mass of LiCoO$_2$, 5 parts by mass of acetylene black, and 5 parts by mass of polyvinylidene fluoride were kneaded in N-methylpyrrolidinone as a solvent, and thus a positive electrode mixture slurry in a paste form was prepared.

Next, this positive electrode mixture slurry was applied on a strip-shaped positive electrode current collector made of an aluminum foil having a thickness of 20 μm, and the slurry was dried. Subsequently, the assembly was compressed with a roll press, and thus a sheet-like positive electrode composed of a positive electrode current collector and a positive electrode active material layer was obtained. The coating density of the positive electrode active material layer in this case was 30 mg/cm$^2$, and the packing density was 2.5 g/ml.

Preparation of Non-Aqueous Electrolyte Solution

In a mixture of ethylene carbonate (EC), dimethyl carbonate (DMC) and methyl ethyl carbonate (EMC) at proportions of 34:33:33 (mass ratio) as a non-aqueous solvent, LiPF$_6$ as an electrolyte was dissolved such that the electrolyte concentration in the finally obtainable non-aqueous electrolyte solution would be 1 mol/liter.

To the solution thus obtained, the cyclic sulfate compound [exemplary compound 1] obtained in Synthesis Example 1 was added as an additive such that the content relative to the total mass of the non-aqueous electrolyte solution would be 0.5 mass %, and thus a non-aqueous electrolyte solution was obtained.

Preparation of Coin Cell

The negative electrode described above was punched into a disc form having a diameter of 14 mm, while the positive electrode described above was punched into a disc form having a diameter of 13 mm, and thus coin-shaped electrodes (a negative electrode and a positive electrode) were obtained. Furthermore, a finely porous polyethylene film having a thickness of 20 μm was punched into a disc form having a diameter of 17 mm, and thus a separator was obtained.

The coin-shaped negative electrode, the separator and the coin-shaped positive electrode thus obtained were laminated in this order inside a battery can (size 2032) made of stainless steel, and 20 μl of a non-aqueous electrolyte solution was injected therein to impregnate the separator, the positive electrode, and the negative electrode.

Furthermore, an aluminum plate (thickness: 1.2 mm, diameter: 16 mm) and a spring were mounted on the positive electrode, a gasket made of polypropylene was inserted, and the battery was sealed by caulking with the battery can lid. Thus, a coin type lithium secondary battery (hereinafter, may be referred to as a "coin cell" or a "test battery") having a diameter of 20 mm and a height of 3.2 mm and having the configuration illustrated in FIG. 1 was prepared.

The coin cell (a test battery) thus obtained was subjected to an evaluation of charge-discharge characteristics and the measurement of open circuit voltage.

[Evaluation Method]

<Evaluation of Charge-Discharge Characteristics of Battery>

A test battery was subjected to a cycle of charging at a constant current of 1 mA and a constant voltage of 4.2 V in a constant temperature chamber at 25° C., and discharging to 2.85 V at a constant current of 1 mA in this constant temperature chamber at 25° C., for 10 cycles. At that time, initial charge-discharge efficiency was calculated from the charge capacity [mAh] and the discharge capacity [mAh] of the first cycle, by the following formula.

The results thus obtained are presented in Table 1.

Initial charge–discharge efficiency[%]=Discharge capacity of first cycle [mAh]/charge capacity of first cycle [mAh]×100[%]

Furthermore, the coin cell was charged at a constant voltage of 4.2 V, and the charged coin cell was stored in a constant temperature chamber at 80° C. for 3 days (hereinafter, this operation will be referred to as a "high temperature storage test"). Subsequently, the discharge capacity [mAh] after the high temperature storage test was measured by the same method as that used for initial discharge capacity, and the capacity retention after the high temperature storage test was calculated by the following formula.

The results thus obtained are presented in Table 1.

Capacity retention[%] after high storage temperature test=Discharge capacity [mAh] after high temperature storage test/discharge capacity of first cycle [mAh]×100

<Measurement of Open Circuit Voltage of Battery>

The open circuit voltage after the high temperature storage test was measured, and the open circuit voltage deterioration degree was calculated by the following formula.

The open circuit voltage deterioration degree thus obtained was compared with the open circuit voltage deterioration degree of [Comparative Example 1-1] that will be described below, with the latter open circuit voltage deterioration degree being defined as 100.

Table 1 indicates the open circuit voltage deterioration degree (relative values) obtained relative to the open circuit voltage deterioration degree of [Comparative Example 1-1] which was taken as 100.

Open circuit voltage deterioration degree[%]=(4.2−open circuit voltage after high temperature storage test [V])/4.2×100[%]

Example 1-2

A coin cell was obtained in the same manner as in Example 1-1, except that the amount of addition of the cyclic sulfate compound [exemplary compound 1] used in the preparation of the non-aqueous electrolyte solution was changed such that the content relative to the total mass of the non-aqueous electrolyte solution would be 0.2 mass %.

The coin cell thus obtained was subjected to an evaluation of the charge-discharge characteristics and the measurement of the open circuit voltage in the same manner as in Example 1-1.

The evaluation results are presented in Table 1.

Example 1-3

A coin cell was obtained in the same manner as in Example 1-1, except that the amount of addition of the cyclic sulfate compound [exemplary compound 1] used in the preparation of the non-aqueous electrolyte solution was changed such that the content relative to the total mass of the non-aqueous electrolyte solution would be 1.0 mass %.

The coin cell thus obtained was subjected to an evaluation of the charge-discharge characteristics and the measurement of the open circuit voltage in the same manner as in Example 1-1.

The evaluation results are presented in Table 1.

Example 1-4

A coin cell was obtained in the same manner as in Example 1-1, except that the amount of addition of the cyclic sulfate compound [exemplary compound 1] used in the preparation of the non-aqueous electrolyte solution was changed such that the content relative to the total mass of the non-aqueous electrolyte solution would be 1.5 mass %.

The coin cell thus obtained was subjected to an evaluation of the charge-discharge characteristics and the measurement of the open circuit voltage in the same manner as in Example 1-1.

The evaluation results are presented in Table 1.

Example 1-5

A coin cell was obtained in the same manner as in Example 1-1, except that the [exemplary compound 2] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to an evaluation of the charge-discharge characteristics and the measurement of the open circuit voltage in the same manner as in Example 1-1.

The evaluation results are presented in Table 1.

Example 1-6

A coin cell was obtained in the same manner as in Example 1-1, except that the [exemplary compound 16] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to an evaluation of the charge-discharge characteristics and the measurement of the open circuit voltage in the same manner as in Example 1-1.

The evaluation results are presented in Table 1.

Example 1-7

A coin cell was obtained in the same manner as in Example 1-1, except that the [exemplary compound 22a] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to an evaluation of the charge-discharge characteristics and the measurement of the open circuit voltage in the same manner as in Example 1-1.

The evaluation results are presented in Table 1.

Example 1-8

A coin cell was obtained in the same manner as in Example 1-7, except that the amount of addition of the cyclic sulfate compound [exemplary compound 22a] used in the preparation of the non-aqueous electrolyte solution such that the content relative to the total mass of the non-aqueous electrolyte solution would be 0.2 mass %.

The coin cell thus obtained was subjected to an evaluation of the charge-discharge characteristics and the measurement of the open circuit voltage in the same manner as in Example 1-1.

The evaluation results are presented in Table 1.

Example 1-9

A coin cell was obtained in the same manner as in Example 1-7, except that the amount of addition of the cyclic sulfate compound [exemplary compound 22a] used in the preparation of the non-aqueous electrolyte solution such that the content relative to the total mass of the non-aqueous electrolyte solution would be 1.0 mass %.

The coin cell thus obtained was subjected to an evaluation of the charge-discharge characteristics and the measurement of the open circuit voltage in the same manner as in Example 1-1.

The evaluation results are presented in Table 1.

Example 1-10

A coin cell was obtained in the same manner as in Example 1-7, except that the amount of addition of the cyclic sulfate compound [exemplary compound 22a] used in the preparation of the non-aqueous electrolyte solution such that the content relative to the total mass of the non-aqueous electrolyte solution would be 1.5 mass %.

The coin cell thus obtained was subjected to an evaluation of the charge-discharge characteristics and the measurement of the open circuit voltage in the same manner as in Example 1-1.

The evaluation results are presented in Table 1.

Example 1-11

A coin cell was obtained in the same manner as in Example 1-7, except that the amount of addition of the cyclic sulfate compound [exemplary compound 22a] used in the preparation of the non-aqueous electrolyte solution such that the content relative to the total mass of the non-aqueous electrolyte solution would be 2.0 mass %.

The coin cell thus obtained was subjected to an evaluation of the charge-discharge characteristics and the measurement of the open circuit voltage in the same manner as in Example 1-1.

The evaluation results are presented in Table 1.

Example 1-12

A coin cell was obtained in the same manner as in Example 1-1, except that the [exemplary compound 22b] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to an evaluation of the charge-discharge characteristics and the measurement of the open circuit voltage in the same manner as in Example 1-1.

The evaluation results are presented in Table 1.

Comparative Example 1-1

A coin cell was obtained in the same manner as in Example 1-1, except that the cyclic sulfate compound [exemplary compound 1] used in the preparation of the non-aqueous electrolyte solution was not added.

The coin cell thus obtained was subjected to an evaluation of the charge-discharge characteristics and the measurement of the open circuit voltage in the same manner as in Example 1-1.

The evaluation results are presented in Table 1.

Comparative Example 1-2

A coin cell was obtained in the same manner as in Example 1-1, except that the following comparative compound 1 was added as the cyclic sulfate instead of the cyclic sulfate compound [exemplary compound 1] used in the preparation of the non-aqueous electrolyte solution such that the content relative to the total mass of the non-aqueous electrolyte solution would be 0.5 mass %. The comparative compound 1 is a cyclic sulfate compound which is not included in the scope of the invention (hereinafter, also referred to as a "comparative cyclic sulfate compound").

The coin cell thus obtained was subjected to an evaluation of the charge-discharge characteristics and the measurement of the open circuit voltage in the same manner as in Example 1-1.

The evaluation results are presented in Table 1.

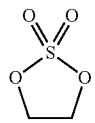

Comparative Compound 1

Comparative Example 1-3

A coin cell was obtained in the same manner as in Example 1-1, except that a comparative compound 2 was added as the cyclic sulfate instead of the cyclic sulfate compound [exemplary compound 1] used in the preparation of the non-aqueous electrolyte solution such that the content relative to the total mass of the non-aqueous electrolyte solution would be 0.5 mass %. The comparative compound 2 is a cyclic sulfate compound which is not included in the scope of the invention (a comparative cyclic sulfate compound).

The coin cell thus obtained was subjected to an evaluation of the charge-discharge characteristics and the measurement of the open circuit voltage in the same manner as in Example 1-1.

The evaluation results are presented in Table 1.

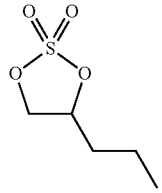

Comparative Compound 2

TABLE 1

| | Additive for non-aqueous electrolyte solution | | Performance evaluation | | |
| --- | --- | --- | --- | --- | --- |
| | Cyclic sulfate compound | Content (mass %) | Initial efficiency [%] | Capacity retention after high temperature storage test [%] | Open circuit voltage deterioration degree (*1) |
| Example 1-1 | Exemplary compound 1 | 0.5 | 91 | 91 | 89 |
| Example 1-2 | | 0.2 | 91 | 91 | 87 |
| Example 1-3 | | 1.0 | 91 | 90 | 88 |
| Example 1-4 | | 1.5 | 91 | 90 | 88 |
| Example 1-5 | Exemplary compound 2 | 0.5 | 92 | 93 | 81 |

TABLE 1-continued

| | Additive for non-aqueous electrolyte solution | | Performance evaluation | | |
|---|---|---|---|---|---|
| | Cyclic sulfate compound | Content (mass %) | Initial efficiency [%] | Capacity retention after high temperature storage test [%] | Open circuit voltage deterioration degree (*1) |
| Example 1-6 | Exemplary compound 16 | 0.5 | 91 | 93 | 87 |
| Example 1-7 | Exemplary compound 22a | 0.5 | 92 | 90 | 94 |
| Example 1-8 | | 0.2 | 92 | 89 | 86 |
| Example 1-9 | | 1.0 | 93 | 90 | 87 |
| Example 1-10 | | 1.5 | 92 | 91 | 92 |
| Example 1-11 | | 2.0 | 93 | 90 | 93 |
| Example 1-12 | Exemplary compound 22b | 0.5 | 93 | 87 | 82 |
| Comparative Example 1-1 | None | — | 91 | 85 | 100 |
| Comparative Example 1-2 | Comparative compound 1 | 0.5 | 92 | 93 | 148 |
| Comparative Example 1-3 | Comparative compound 2 | 0.5 | 91 | 92 | 123 |

(*1) The "open circuit voltage deterioration degree" is a relative value with respect to the open circuit voltage deterioration degree (%) of Comparative Example 1-1, which is defined as 100.

As indicated in Table 1, in Examples 1-1 to 1-12, initial efficiency was maintained, and the capacity retention was improved, while a decrease in the open circuit voltage after the high temperature storage test was suppressed, as compared with Comparative Example 1-1 that did not contain a cyclic sulfate compound.

On the other hand, in Comparative Examples 1-2 and 1-3 in which the comparative compounds 1 and 2, which were comparative cyclic sulfate compounds, were added, an increase in the open circuit voltage deterioration degree after the high temperature storage test was confirmed.

Example 2-1

A lithium secondary battery was prepared by the following procedure.

Preparation of Negative Electrode

A negative electrode was prepared in the same manner as in Example 1-1.

Preparation of Positive Electrode

A positive electrode mixture slurry in a paste form was prepared in the same manner as in Example 1-1, except that LiMnO$_2$ was used instead of LiCoO$_2$ of Example 1-1.

Next, this positive electrode mixture slurry was applied on a strip-shaped positive electrode current collector made of an aluminum foil having a thickness of 20 μm, and the slurry was dried. Subsequently, the assembly was compressed with a roll press, and thus a sheet-like positive electrode composed of a positive electrode current collector and a positive electrode active material was obtained. The coating density of a positive electrode active material layer in this case was 32 mg/cm$^2$, and the packing density was 2.7 g/ml.

Preparation of Non-Aqueous Electrolyte Solution

In a mixture of ethylene carbonate (EC), dimethyl carbonate (DMC) and methyl ethyl carbonate (EMC) at proportions of 34:33:33 (mass ratio) as a non-aqueous solvent, LiPF$_6$ as an electrolyte was dissolved such that the electrolyte concentration in the finally obtainable non-aqueous electrolyte solution would be 1 mol/liter.

To the solution thus obtained, the cyclic sulfate compound [exemplary compound 1] obtained in Synthesis Example 1 described above and vinylene carbonate (VC) were added as additives such that their contents relative to the total mass of the non-aqueous electrolyte solution would be respectively 1.0 mass %, and thus a non-aqueous electrolyte solution was obtained.

Preparation of Coin Cell

A coin cell was prepared in the same manner as in Example 1-1, except that the positive electrode and the non-aqueous electrolyte solution used in Example 1-1 were changed to the positive electrode and the non-aqueous electrolyte solution obtained as described above.

Evaluation of Battery

The coin cell thus obtained was subjected to an evaluation of the charge-discharge characteristics and the measurement of the open circuit voltage in the same manner as in Example 1-1.

The evaluation results are presented in Table 2.

Example 2-2

A coin cell was obtained in the same manner as in Example 2-1, except that the [exemplary compound 22a] was added instead of the cyclic sulfate compound [exemplary compound 1] used in the preparation of the non-aqueous electrolyte solution such that the content relative to the total mass of the non-aqueous electrolyte solution would be 1.0 mass %.

The coin cell thus obtained was subjected to an evaluation of the charge-discharge characteristics and the measurement of the open circuit voltage in the same manner as in Example 2-1.

The evaluation results are presented in Table 2.

Comparative Example 2-1

A coin cell was obtained in the same manner as in Example 2-1, except that the cyclic sulfate compound [exemplary compound 1] used in the preparation of the non-aqueous electrolyte solution was not added.

The coin cell thus obtained was subjected to an evaluation of the charge-discharge characteristics and the measurement of the open circuit voltage in the same manner as in Example 2-1.

The evaluation results are presented in Table 2.

Comparative Example 2-2

A coin cell was obtained in the same manner as in Example 2-1, except that the comparative compound 1 was added as the cyclic sulfate instead of the cyclic sulfate compound [exemplary compound 1] used in the preparation of the non-aqueous electrolyte solution such that the content relative to the total mass of the non-aqueous electrolyte solution would be 1.0 mass %. The comparative compound 1 is a cyclic sulfate compound which is not included in the scope of the invention.

The coin cell thus obtained was subjected to an evaluation of the charge-discharge characteristics and the measurement of the open circuit voltage in the same manner as in Example 2-1.

The evaluation results are presented in Table 2.

Comparative Example 2-3

A coin cell was obtained in the same manner as in Example 2-1, except that the comparative compound 2 was added as the cyclic sulfate instead of the cyclic sulfate compound [exemplary compound 1] used in the preparation of the non-aqueous electrolyte solution such that the content relative to the total mass of the non-aqueous electrolyte solution would be 1.0 mass %. The comparative compound 2 is a cyclic sulfate compound which is not included in the scope of the invention.

The coin cell thus obtained was subjected to an evaluation of the charge-discharge characteristics and the measurement of the open circuit voltage in the same manner as in Example 2-1.

The evaluation results are presented in Table 2.

the open circuit voltage deterioration degree after the high temperature storage test was confirmed.

Example 3-1

A lithium secondary battery was prepared by the following procedure.

Preparation of Negative Electrode

A negative electrode was prepared in the same manner as in Example 1-1.

Preparation of Positive Electrode

A positive electrode was prepared in the same manner as in Example 2-1.

Preparation of Non-Aqueous Electrolyte Solution

A non-aqueous electrolyte solution was obtained in the same manner as in Example 2-1, except that fluoroethylene carbonate (FEC) was used instead of vinylene carbonate.

Preparation of Coin Cell

A coin cell was prepared in the same manner as in Example 2-1, except that the non-aqueous electrolyte solution used in Example 2-1 was changed to the non-aqueous electrolyte solution obtained as described above.

<Evaluation of Battery>

The coin cell thus obtained was subjected to an evaluation of the charge-discharge characteristics and the measurement of the open circuit voltage in the same manner as in Example 2-1.

The evaluation results are presented in Table 3.

Example 3-2

A coin type lithium secondary battery was obtained in the same manner as in Example 3-1, except that the [exemplary

TABLE 2

| | Additive for non-aqueous electrolyte solution | | | | Performance evaluation | | |
| --- | --- | --- | --- | --- | --- | --- | --- |
| | Cyclic sulfate compound | Content (mass %) | Additive used in combination | Content (mass %) | Initial efficiency [%] | Capacity retention after high temperature storage test [%] | Open circuit voltage deterioration degree (*1) |
| Example 2-1 | Exemplary compound 1 | 1.0 | VC | 1.0 | 92 | 89 | 80 |
| Example 2-2 | Exemplary compound 22a | 1.0 | VC | 1.0 | 92 | 86 | 86 |
| Comparative Example 2-1 | None | — | VC | 1.0 | 91 | 83 | 92 |
| Comparative Example 2-2 | Comparative compound 1 | 1.0 | VC | 1.0 | 92 | 79 | 107 |
| Comparative Example 2-3 | Comparative compound 2 | 1.0 | VC | 1.0 | 91 | 77 | 112 |

(*1) The "open circuit voltage deterioration degree" is a relative value with respect to the open circuit voltage deterioration degree (%) of Comparative Example 1-1, which is defined as 100.

As indicated in Table 2, in Examples 2-1 and 2-2, initial efficiency was maintained, and the capacity retention was improved, while a decrease in the open circuit voltage after the high temperature storage test was suppressed, as compared with Comparative Example 2-1 that did not contain a cyclic sulfate compound.

On the other hand, in Comparative Examples 2-2 and 2-3 in which the comparative compounds 1 and 2, which were comparative cyclic sulfate compounds, were added, an increase in compound 22a] was added instead of the cyclic sulfate compound [exemplary compound 1] used in the preparation of the non-aqueous electrolyte solution such that the content relative to the total mass of the non-aqueous electrolyte solution would be 1.0 mass %.

The coin cell thus obtained was subjected to an evaluation of the charge-discharge characteristics and the measurement of the open circuit voltage in the same manner as in Example 3-1.

The evaluation results are presented in Table 3.

Comparative Example 3-1

A coin cell was obtained in the same manner as in Example 3-1, except that the cyclic sulfate compound [exemplary compound 1] used in the preparation of the non-aqueous electrolyte solution was not added.

The coin cell thus obtained was subjected to an evaluation of the charge-discharge characteristics and the measurement of the open circuit voltage in the same manner as in Example 3-1.

The evaluation results are presented in Table 3.

Comparative Example 3-2

A coin cell was obtained in the same manner as in Example 3-1, except that the comparative compound 1 was added as the cyclic sulfate instead of the cyclic sulfate compound [exemplary compound 1] used in the preparation of the non-aqueous electrolyte solution such that the content relative to the total mass of the non-aqueous electrolyte solution would be 1.0 mass %. The comparative compound 1 is a cyclic sulfate compound which is not included in the scope of the invention.

The coin cell thus obtained was subjected to an evaluation of the charge-discharge characteristics and the measurement of the open circuit voltage in the same manner as in Example 3-1.

The evaluation results are presented in Table 3.

Comparative Example 3-3

A coin cell was obtained in the same manner as in Example 3-1, except that the comparative compound 2 was added as the cyclic sulfate instead of the cyclic sulfate compound [exemplary compound 1] used in the preparation of the non-aqueous electrolyte solution such that the content relative to the total mass of the non-aqueous electrolyte solution would be 1.0 mass %. The comparative compound 2 is a cyclic sulfate compound which is not included in the scope of the invention.

The coin cell thus obtained was subjected to an evaluation of the charge-discharge characteristics and the measurement of the open circuit voltage in the same manner as in Example 3-1.

The evaluation results are presented in Table 3.

As indicated in Table 3, in Examples 3-1 and 3-2, initial efficiency was maintained, and the capacity retention was improved, while a decrease in the open circuit voltage after the high temperature storage test was suppressed, as compared with Comparative Example 3-1 that did not contain a cyclic sulfate compound.

On the other hand, in Comparative Examples 3-2 and 3-3 in which the comparative compounds 1 and 2, which were comparative cyclic sulfate compounds, were added, an increase in the open circuit voltage deterioration degree after the high temperature storage test was confirmed.

Example 4-1

A lithium secondary battery was prepared by the following procedure.

Preparation of Negative Electrode

A negative electrode was prepared in the same manner as in Example 1-1.

Preparation of Positive Electrode

A positive electrode was prepared in the same manner as in Example 1-1.

Preparation of Non-Aqueous Electrolyte Solution

In a mixture of ethylene carbonate (EC), dimethyl carbonate (DMC) and methyl ethyl carbonate (EMC) at proportions of 34:33:33 (mass ratio) as a non-aqueous solvent, $LiPF_6$ as an electrolyte was dissolved such that the electrolyte concentration in the finally obtainable non-aqueous electrolyte solution would be 1 mol/liter.

To the solution thus obtained, the cyclic sulfate compound [exemplary compound 1] obtained in Synthesis Example 1 described above, and as an electrolyte compound represented by formula (V), a compound represented by formula (VIII) with M described above being lithium, were added as an additive such that the contents relative to the total mass of the non-aqueous electrolyte solution would be respectively 0.5 mass %, and thus a non-aqueous electrolyte solution was obtained.

Meanwhile, in Table 4 described below, the electrolyte compound represented by formula (V) is indicated as a "compound of formula (V)", and a compound represented by formula (VIII) with M being lithium is indicated as "formula (VIII) (M=Li)".

TABLE 3

| | Additive for non-aqueous electrolyte solution | | | | Performance evaluation | | |
|---|---|---|---|---|---|---|---|
| | Cyclic sulfate compound | Content (mass %) | Additive used in combination | Content (mass %) | Initial efficiency [%] | Capacity retention after high temperature storage test [%] | Open circuit voltage deterioration degree (*1) |
| Example 3-1 | Exemplary compound 1 | 1.0 | FEC | 1.0 | 91 | 88 | 87 |
| Example 3-2 | Exemplary compound 22a | 1.0 | FEC | 1.0 | 92 | 86 | 89 |
| Comparative Example 3-1 | None | — | FEC | 1.0 | 92 | 76 | 105 |
| Comparative Example 3-2 | Comparative compound 1 | 1.0 | FEC | 1.0 | 92 | 80 | 114 |
| Comparative Example 3-3 | Comparative compound 2 | 1.0 | FEC | 1.0 | 92 | 79 | 126 |

(*1) The "open circuit voltage deterioration degree" is a relative value with respect to the open circuit voltage deterioration degree (%) of Comparative Example 1-1, which is defined as 100.

Preparation of Coin Cell

A coin cell was prepared in the same manner as in Example 1-1, except that the non-aqueous electrolyte solution used in Example 1-1 was changed to the non-aqueous electrolyte solution obtained as described above.

The coin cell (test battery) thus obtained was subjected to an evaluation as described below.

[Evaluation Method]

<Measurement of Initial Characteristics and Initial Resistance Value (−20° C.) of Battery>

As an evaluation of the initial characteristics of the battery, the initial resistance value (−20° C.) was measured in the manner described below. A lower initial resistance value (−20° C.) is more satisfactory.

Each of the coin type batteries was charged at a constant voltage of 4.0 V, and then the charged coin cell was cooled to −20° C. in a constant temperature chamber. The coin cell was discharged at a constant current of 0.2 mA at −20° C., and the decrease in potential for 10 seconds from the initiation of discharge was measured. Thereby, the direct current resistance [Ω] of the coin cell was measured, and this value was defined as the initial resistance value (−20° C.). For the initial resistance value (−20° C.) thus obtained, a relative value was determined with respect to the initial resistance value of [Comparative Example 1-1], which was defined as 100.

The relative values of the initial resistance value (−20° C.) are presented in Table 4.

In regard to the storage characteristics of the battery, the capacity retention, open circuit voltage deterioration degree, and resistance retention ratio described below were evaluated. Here, as the capacity retention is higher, the retention characteristics of the battery are more satisfactory; as the open circuit voltage deterioration degree is lower, the retention characteristics of the battery are more satisfactory; and as the resistance retention ratio is lower, the retention characteristics of the battery are more satisfactory.

<Measurement of Capacity Retention as Storage Characteristics of Battery>

The capacity retention of the coin type batteries were measured in the same manner as in the case of the "capacity retention [%] after high temperature storage test" in Example 1-1.

The results thus obtained are presented in Table 4.

<Measurement of Open Circuit Voltage Deterioration Degree as Storage Characteristics of Battery>

The open circuit voltage deterioration degree of the coin type batteries was measured in the same manner as in the case of the "open circuit voltage deterioration degree [%] of battery" in Example 1-1.

The results thus obtained are presented in Table 4.

<Measurement of Resistance Retention Ratio (−20° C.) as Storage Characteristics of Battery>

A coin cell after the measurement of the initial resistance value was charged at a constant voltage of 4.2 V, and the charged coin cell was stored for 3 days in a constant temperature chamber at 80° C. (hereinafter, this operation will be referred to as a "high temperature storage test"). Subsequently, the resistance value after the high temperature storage test was measured by the same method as that used for the initial resistance value (−20° C.) (that is, under the conditions of −20° C.), and thus the resistance retention ratio (−20° C.) of the battery was calculated by the following formula.

The results thus obtained are presented in Table 4.

Storage characteristics, resistance retention ratio (−20° C.)=(Resistance value [Ω] after high temperature storage test/initial resistance value [Ω])/(resistance value [Ω] after high temperature storage in Comparative Example 1-1/initial resistance value [Ω] in Comparative Example 1-1)

Example 4-2

A coin cell was obtained in the same manner as in Example 4-1, except that the [exemplary compound 22a] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to various analyses in the same manner as in Example 4-1. The evaluation results are presented in Table 4.

Example 4-3

A coin cell was obtained in the same manner as in Example 4-1, except that the [exemplary compound 22b] was added instead of the cyclic sulfate compound [exemplary compound 1] used in the preparation of the non-aqueous electrolyte solution such that the content relative to the total mass of the non-aqueous electrolyte solution would be 0.5 mass %.

The coin cell thus obtained was subjected to various analyses in the same manner as in Example 4-1. The evaluation results are presented in Table 4.

Comparative Example 1-1

A coin cell of Comparative Example 1-1 was obtained by the method described above. Meanwhile, the non-aqueous electrolyte solution for Comparative Example 1-1 contained neither the cyclic sulfate compound represented by formula (I) nor the electrolyte compound represented by formula (V).

The coin cell thus obtained was subjected to various analyses in the same manner as in Example 4-1. The evaluation results are presented in Table 4.

Comparative Example 4-1

A coin cell was obtained in the same manner as in Example 4-1, except that the cyclic sulfate compound [exemplary compound 1] used in the preparation of the non-aqueous electrolyte solution was not added.

The coin cell thus obtained was subjected to various analyses in the same manner as in Example 4-1. The evaluation results are presented in Table 4.

TABLE 4

| | Additive for non-aqueous electrolyte solution | | | | Initial characteristics | Storage characteristics | | |
| --- | --- | --- | --- | --- | --- | --- | --- | --- |
| | Cyclic sulfate compound | Content (mass %) | Compound of formula (V) | Content (mass %) | Initial resistance value (−20° C.) (*1) | Capacity retention [%] | Open circuit voltage deterioration degree (*2) | Resistance retention ratio (−20° C.) |
| Example 4-1 | Exemplary compound 1 | 0.5 | Formula (VIII) (M = Li) | 0.5 | 95 | 91 | 92 | 0.90 |
| Example 4-2 | Exemplary compound 22a | 0.5 | Formula (VIII) (M = Li) | 0.5 | 92 | 90 | 97 | 0.93 |

TABLE 4-continued

| | Additive for non-aqueous electrolyte solution | | | | Initial characteristics | Storage characteristics | | |
|---|---|---|---|---|---|---|---|---|
| | Cyclic sulfate compound | Content (mass %) | Compound of formula (V) | Content (mass %) | Initial resistance value (−20° C.) (*1) | Capacity retention [%] | Open circuit voltage deterioration degree (*2) | Resistance retention ratio (−20° C.) |
| Example 4-3 | Exemplary compound 22b | 0.5 | Formula (VIII) (M = Li) | 0.5 | 92 | 90 | 97 | 0.93 |
| Comparative Example 1-1 | None | — | None | — | 100 | 85 | 100 | 1.00 |
| Comparative Example 4-1 | None | — | Formula (VIII) (M = Li) | 0.5 | 87 | 85 | 106 | 1.08 |

(*1) The "resistance value (−20° C.)" as an initial characteristic is a relative value with respect to the initial resistance value of Comparative Example 1-1, which is defined as 100.
(*2) The "open circuit voltage deterioration degree" as a storage characteristic is a relative value with respect to the open circuit voltage deterioration degree (%) of Comparative Example 1-1, which is defined as 100.

As indicated in Table 4, in Examples 4-1 to 4-3, the low temperature resistance value as an initial characteristic was significantly reduced, and the capacity retention, the open circuit voltage deterioration degree, and the low temperature resistance retention ratio as storage characteristics were significantly improved, as compared with Comparative Example 1-1 that did not contain any additive.

On the other hand, as shown in Comparative Example 4-1, when only the electrolyte compound represented by formula (V) was added, it is effective in the reduction of the low temperature resistance value as an initial characteristic, but sufficient effects cannot be obtained for the general storage characteristics.

Example 5-1

A lithium secondary battery was prepared by the following procedure.

Preparation of Negative Electrode

A negative electrode was prepared in the same manner as in Example 1-1.

Preparation of Positive Electrode

A positive electrode was prepared in the same manner as in Example 1-1.

Preparation of Non-Aqueous Electrolyte Solution

In a mixture of ethylene carbonate (EC), dimethyl carbonate (DMC) and methyl ethyl carbonate (EMC) at proportions of 34:33:33 (mass ratio) as a non-aqueous solvent, $LiPF_6$ as an electrolyte was dissolved such that the electrolyte concentration in the finally obtainable non-aqueous electrolyte solution would be 1 mol/liter.

To the solution thus obtained, the cyclic sulfate compound [exemplary compound 22a] obtained in Synthesis Example 1 described above and lithium difluorophosphate $(LiOP(O)F_2)$ were added as additives such that their contents relative to the total mass of the non-aqueous electrolyte solution would be respectively 0.5 mass %, and thus a non-aqueous electrolyte solution was obtained.

Preparation of Coin Cell

A coin cell was prepared in the same manner as in Example 1-1, except that the non-aqueous electrolyte solution used in Example 1-1 was changed to the non-aqueous electrolyte solution obtained as described above.

The coin cell (test battery) thus obtained was subjected to an evaluation in the same manner as in Example 4-1. The evaluation results are presented in Table 5.

Comparative Example 1-1

A coin cell of Comparative Example 1-1 was obtained by the method described above. Meanwhile, the non-aqueous electrolyte solution for Comparative Example 1-1 contained neither the cyclic sulfate compound represented by formula (I) nor lithium difluorophosphate $(LiOP(O)F_2)$.

The coin cell thus obtained was subjected to various analyses in the same manner as in Example 5-1. The evaluation results are presented in Table 5.

Comparative Example 5-1

A coin cell was obtained in the same manner as in Example 5-1, except that the cyclic sulfate compound [exemplary compound 22a] used in the preparation of the non-aqueous electrolyte solution was not added.

The coin cell thus obtained was subjected to various analyses in the same manner as in Example 5-1. The evaluation results are presented in Table 5.

TABLE 5

| | Additive for non-aqueous electrolyte solution | | | Initial characteristics | Storage characteristics | | |
|---|---|---|---|---|---|---|---|
| | Cyclic sulfate compound | Content (mass %) | Content of $LiOP(O)F_2$ (mass %) | Initial resistance value (−20° C.) (*1) | Capacity retention [%] | Open circuit voltage deterioration degree (*2) | Resistance retention ratio (−20° C.) |
| Example 5-1 | Exemplary compound 22a | 0.5 | 0.5 | 87 | 88 | 92 | 0.93 |

TABLE 5-continued

| | Additive for non-aqueous electrolyte solution | | Initial characteristics | Storage characteristics | | |
|---|---|---|---|---|---|---|
| | Cyclic sulfate compound | Content (mass %) | Content of LiOP(O)F$_2$ (mass %) | Initial resistance value (−20° C.) (*1) | Capacity retention [%] | Open circuit voltage deterioration degree (*2) | Resistance retention ratio (−20° C.) |
| Comparative Example 1-1 | None | — | None | 100 | 85 | 100 | 1.00 |
| Comparative Example 5-1 | None | — | 0.5 | 80 | 81 | 126 | 1.12 |

(*1) The "resistance value (−20° C.)" as an initial characteristic is a relative value with respect to the initial resistance value of Comparative Example 1-1, which is defined as 100.
(*2) The "open circuit voltage deterioration degree" as a storage characteristic is a relative value with respect to the open circuit voltage deterioration degree (%) of Comparative Example 1-1, which is defined as 100.

As indicated in Table 5, in Example 5-1, the low temperature resistance value as an initial characteristic was significantly reduced, and the capacity retention and the open circuit voltage deterioration degree as storage characteristics were satisfactorily maintained while the low temperature resistance retention ratio was significantly improved, as compared with Comparative Example 1-1 that did not contain any additive.

On the other hand, as shown in Comparative Example 5-1, when only the electrolyte compound represented by LiOP(O)F$_2$ was added, it is effective in the reduction of the low temperature resistance value as an initial characteristic, but sufficient effects cannot be obtained for the general storage characteristics.

The entire disclosures of Japanese Patent Application No. 2010-237173 and Japanese Patent Application No. 2011-189632 are incorporated in this specification by reference.

All publications, patent applications, and technical standards mentioned in this specification are herein incorporated by reference to the same extent as if each individual publication, patent application, or technical standard was specifically and individually indicated to be incorporated by reference.

The invention claimed is:

1. A non-aqueous electrolyte solution, comprising:
a cyclic sulfate compound represented by the following formula (I):

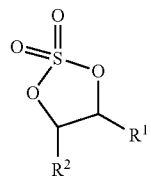

(I)

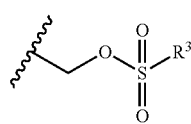

(II)

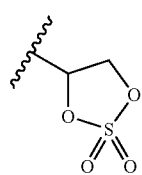

(III)

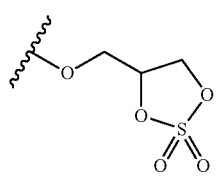

(IV)

wherein, in formula (I), R$^1$ represents a group represented by the above formula (II) or a group represented by the above formula (III); and R$^2$ represents a hydrogen atom, an alkyl group having from 1 to 6 carbon atoms, a group represented by formula (II), or a group represented by formula (III);
in formula (II), R$^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding; and
in a case in which there are two groups represented by formula (II) in the cyclic sulfate compound represented by formula (I), the two groups represented by formula (II) may be the same as or different from each other.

2. The non-aqueous electrolyte solution according to claim 1, wherein in formula (I), R$^1$ represents a group represented by formula (II) (provided that in formula (II), R$^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III); and R$^2$ represents a hydrogen atom, an alkyl group having from 1 to 3 carbon atoms, a group represented by formula (II) (provided that in formula (II), R$^3$ represents a fluorine atom, an alkyl group having from 1 to 3 carbon atoms, a halogenated alkyl group having from 1 to 3 carbon atoms, an alkoxy group having from 1 to 3 carbon atoms, or a group represented by formula (IV)), or a group represented by formula (III).

3. The non-aqueous electrolyte solution according to claim 2, wherein in formula (I), R$^1$ represents a group represented by formula (II) (provided that in formula (II), R$^3$ represents a fluorine atom, a methyl group, an ethyl group, a methoxy group, an ethoxy group, or a group represented by formula (IV)), or a group represented by formula (III); and R$^2$ represents a hydrogen atom or a methyl group.

4. The non-aqueous electrolyte solution according to claim 3, wherein in formula (I), R$^1$ represents a group represented by formula (III), and R$^2$ represents a hydrogen atom.

5. The non-aqueous electrolyte solution according to claim 1, further comprising at least one of an electrolyte compound represented by the following formula (V) or lithium difluorophosphate:

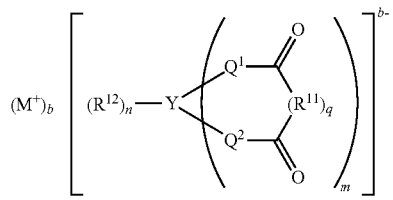

(V)

wherein, in formula (V), M represents an alkali metal; Y represents a transition element, or an element of Group 13, Group 14 or Group 15 of the Periodic Table of Elements; b represents an integer from 1 to 3; m represents an integer from 1 to 4; n represents an integer from 0 to 8; q represents 0 or 1; $R^{11}$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, wherein such groups may each contain a substituent or a heteroatom in the structure, and when q is 1 and m is 2 to 4, m units of $R^{11}$ may be bonded to each other; $R^{12}$ represents a halogen atom, an alkyl group having from 1 to 10 carbon atoms, a halogenated alkyl group having from 1 to 10 carbon atoms, an aryl group having from 6 to 20 carbon atoms, a halogenated aryl group having from 6 to 20 carbon atoms, or $-Q^3R^{13}$, wherein such groups, other than $-Q^3R^{13}$, may each contain a substituent or a heteroatom in the structure, and when n represents an integer from 2 to 8, n units of $R^{12}$ may be bonded to each other to form a ring; $Q^1$, $Q^2$, and $Q^3$ each independently represent O, S or $NR^{14}$; and $R^{13}$ and $R^{14}$ each independently represent a hydrogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, wherein such groups may each contain a substituent or a heteroatom in the structure, and when plural $R^{13}$'s or plural $R^{14}$'s are present, the respective groups may be bonded to each other to form a ring.

6. The non-aqueous electrolyte solution according to claim 5, wherein the electrolyte compound represented by formula (V) is at least one compound selected from the group consisting of a compound represented by the following formula (VI), a compound represented by the following formula (VII), a compound represented by the following formula (VIII), and a compound represented by the following formula (IX):

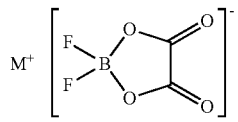

(VI)

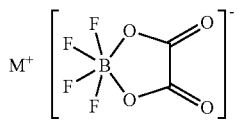

(VII)

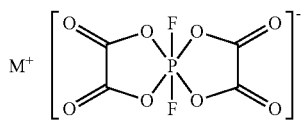

(VIII)

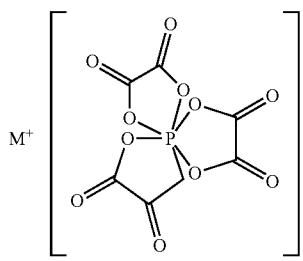

(IX)

wherein, in formulae (VI) to (IX), M has the same definition as M in formula (V).

7. The non-aqueous electrolyte solution according to claim 1, further comprising a compound represented by the following formula (X):

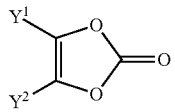

(X)

wherein, in formula (X), $Y^1$ and $Y^2$ each independently represent a hydrogen atom, a methyl group, an ethyl group, or a propyl group.

8. The non-aqueous electrolyte solution according to claim 1, further comprising a compound represented by the following formula (XI):

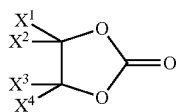

(XI)

wherein, in formula (XI), $X^1$, $X^2$, $X^3$ and $X^4$ each independently represent an alkyl group, having from 1 to 3 carbon atoms, that may be substituted with a fluorine atom; a hydrogen atom; a fluorine atom; or a chlorine atom, provided that $X^1$ to $X^4$ are not both hydrogen atoms at the same time.

9. The non-aqueous electrolyte solution according to claim 1, wherein the content of the cyclic sulfate compound represented by formula (I) is from 0.001 mass % to 10 mass %.

10. The non-aqueous electrolyte solution according to claim 5, wherein the content of at least one of the electrolyte compound represented by formula (V) or the lithium difluorophosphate is from 0.001 mass % to 10 mass %.

11. The non-aqueous electrolyte solution according to claim 7, wherein the content of the compound represented by formula (X) is from 0.001 mass % to 10 mass %.

12. The non-aqueous electrolyte solution according to claim 8, wherein the content of the compound represented by formula (XI) is from 0.001 mass % to 10 mass %.

13. An additive for a lithium secondary battery, the additive comprising a cyclic sulfate compound represented by the following formula (I) as an active ingredient:

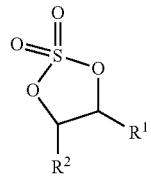
(I)

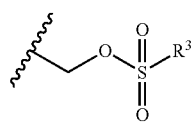
(II)

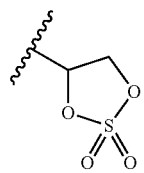
(III)

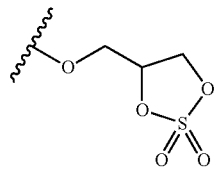
(IV)

wherein, in formula (I), $R^1$ represents a group represented by the above formula (II) or a group represented by the above formula (III); and $R^2$ represents a hydrogen atom, an alkyl group having from 1 to 6 carbon atoms, a group represented by formula (II), or a group represented by formula (III);

in formula (II), $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by the above formula (IV); and the wavy line in formula (II), formula (III) and formula (IV) represents the position of bonding; and in a case in which there are two groups represented by formula (II) in the cyclic sulfate compound represented by formula (I), the two groups represented by formula (II) may be the same as or different from each other.

14. A lithium secondary battery, comprising:
a positive electrode;
a negative electrode including, as a negative electrode active material, at least one selected from metal lithium, a lithium-containing alloy, a metal or alloy capable of alloying with lithium, an oxide capable of doping and dedoping of lithium ions, transition metal nitrides capable of doping and dedoping of lithium ions, or a carbon material capable of doping and dedoping of lithium ions; and
the non-aqueous electrolyte solution according to claim 1.

15. A lithium secondary battery obtained by charging or discharging a lithium secondary battery that includes: a positive electrode; a negative electrode containing, as a negative electrode active material, at least one selected from metal lithium, a lithium-containing alloy, a metal or alloy capable of alloying with lithium, an oxide capable of doping and dedoping of lithium ions, transition metal nitrides capable of doping and dedoping of lithium ions, or a carbon material capable of doping and dedoping of lithium ions; and the non-aqueous electrolyte solution according to claim 1.

16. A cyclic sulfate compound represented by the following formula (XII):

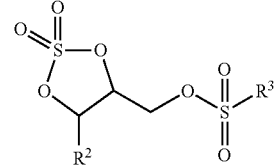
(XII)

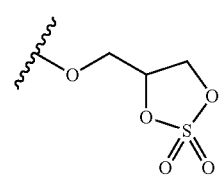
(IV)

wherein, in formula (XII), $R^2$ represents a hydrogen atom or an alkyl group having from 1 to 6 carbon atoms; and $R^3$ represents a halogen atom, an alkyl group having from 1 to 6 carbon atoms, a halogenated alkyl group having from 1 to 6 carbon atoms, an alkoxy group having from 1 to 6 carbon atoms, or a group represented by formula (IV).

17. The cyclic sulfate compound according to claim 16, wherein in formula (XII), $R^2$ represents a hydrogen atom or a methyl group; and $R^3$ represents a fluorine atom, a methyl group, an ethyl group, a methoxy group, an ethoxy group, or a group represented by formula (IV).

18. The cyclic sulfate compound according to claim 16, which is 4-methylsulfonyloxymethyl-2,2-dioxo-1,3,2-dioxathiolane, 4-ethylsulfonyloxymethyl-2,2-dioxo-1,3,2-dioxathiolane, or bis((2,2-dioxo-1,3,2-dioxathiolane-4-yl)methyl) sulfate.

* * * * *